US010004840B2

(12) United States Patent
Zambianchi et al.

(10) Patent No.: US 10,004,840 B2
(45) Date of Patent: Jun. 26, 2018

(54) BLOOD FILTER, SYSTEM AND USE OF A BLOOD FILTER OR SYSTEM

(71) Applicant: FRESENIUS HEMOCARE ITALIA SRL, Cavezzo (IT)

(72) Inventors: Laura Zambianchi, Reggio Emilia (IT); Serena Borghi, Medolla (IT); Giorgio Mari, Morandola (IT)

(73) Assignee: FRESENIUS HEMOCARE ITALIA S.R.L., Cavezzo (IL)

( * ) Notice: Subject to any disclaimer, the term of this patent is extended or adjusted under 35 U.S.C. 154(b) by 278 days.

(21) Appl. No.: 14/353,828

(22) PCT Filed: Jan. 24, 2013

(86) PCT No.: PCT/EP2013/051319
§ 371 (c)(1),
(2) Date: Apr. 24, 2014

(87) PCT Pub. No.: WO2013/110694
PCT Pub. Date: Aug. 1, 2013

(65) Prior Publication Data
US 2014/0299556 A1    Oct. 9, 2014

Related U.S. Application Data

(60) Provisional application No. 61/590,348, filed on Jan. 25, 2012.

(30) Foreign Application Priority Data

Jan. 25, 2012  (EP) .................................... 12152389

(51) Int. Cl.
*A61M 1/34*        (2006.01)
*B01D 39/16*       (2006.01)

(52) U.S. Cl.
CPC ........... *A61M 1/34* (2013.01); *B01D 39/1623* (2013.01); *B01D 2239/064* (2013.01);
(Continued)

(58) Field of Classification Search
CPC .... B01D 2239/0618; B01D 2239/0622; B01D 2239/0627; B01D 2239/064;
(Continued)

(56) References Cited

U.S. PATENT DOCUMENTS 5,057,368 A   10/1991  Largman et al.
5,152,905 A   10/1992  Pall et al.
(Continued)

FOREIGN PATENT DOCUMENTS

WO    WO 98/01207      1/1998
WO    WO 2002/18693    3/2002
WO    WO 2004/050216   6/2004

OTHER PUBLICATIONS

Written Opinion of the International Preliminary Examining Authority dated Jul. 2, 2013, for International Application No. PCT/EP2013/051319.
(Continued)

*Primary Examiner* — John Kim
(74) *Attorney, Agent, or Firm* — Cook Alex Ltd.

(57) ABSTRACT

The invention relates to a blood filter, a system comprising a blood filter and the use of a blood filter or system for the removal of substances from whole blood or blood components.
According to the invention, a blood filter comprises an inlet (2), an outlet (3) and at least first fibers disposed between the inlet (2) and the outlet (3) for filtering a fluid being communicated between the inlet (2) and the outlet (3), wherein each of the first fibers comprises at least one groove extending in the longitudinal direction of the fiber.

17 Claims, 15 Drawing Sheets

(52) U.S. Cl.
CPC ............... *B01D 2239/065* (2013.01); *B01D 2239/0618* (2013.01); *B01D 2239/0622* (2013.01); *B01D 2239/0627* (2013.01); *B01D 2239/1233* (2013.01); *B01D 2239/1291* (2013.01)

(58) Field of Classification Search
CPC ...... B01D 2239/065; B01D 2239/1233; B01D 2239/1291; B01D 39/1623; A61M 1/34
See application file for complete search history.

(56) References Cited

U.S. PATENT DOCUMENTS

| | | | | |
|---|---|---|---|---|
| 5,591,337 | A * | 1/1997 | Lynn | A61J 1/10 156/272.2 |
| 6,231,770 | B1 | 5/2001 | Bormann et al. | |
| 6,649,547 | B1 | 11/2003 | Arnold et al. | |
| 8,293,107 | B1 * | 10/2012 | Lobovsky | B01D 17/0202 210/321.79 |
| 2004/0147194 | A1 | 7/2004 | Willis et al. | |
| 2005/0145561 | A1 * | 7/2005 | Takai | B01D 67/0009 210/500.38 |
| 2009/0130160 | A1 * | 5/2009 | Dugan | A61K 33/38 424/407 |
| 2011/0031184 | A1 * | 2/2011 | Krause | B01D 63/02 210/500.23 |

OTHER PUBLICATIONS

International Search Report and Written Opinion dated Apr. 5, 2013, for International Application No. PCT/EP2013/051319.

\* cited by examiner

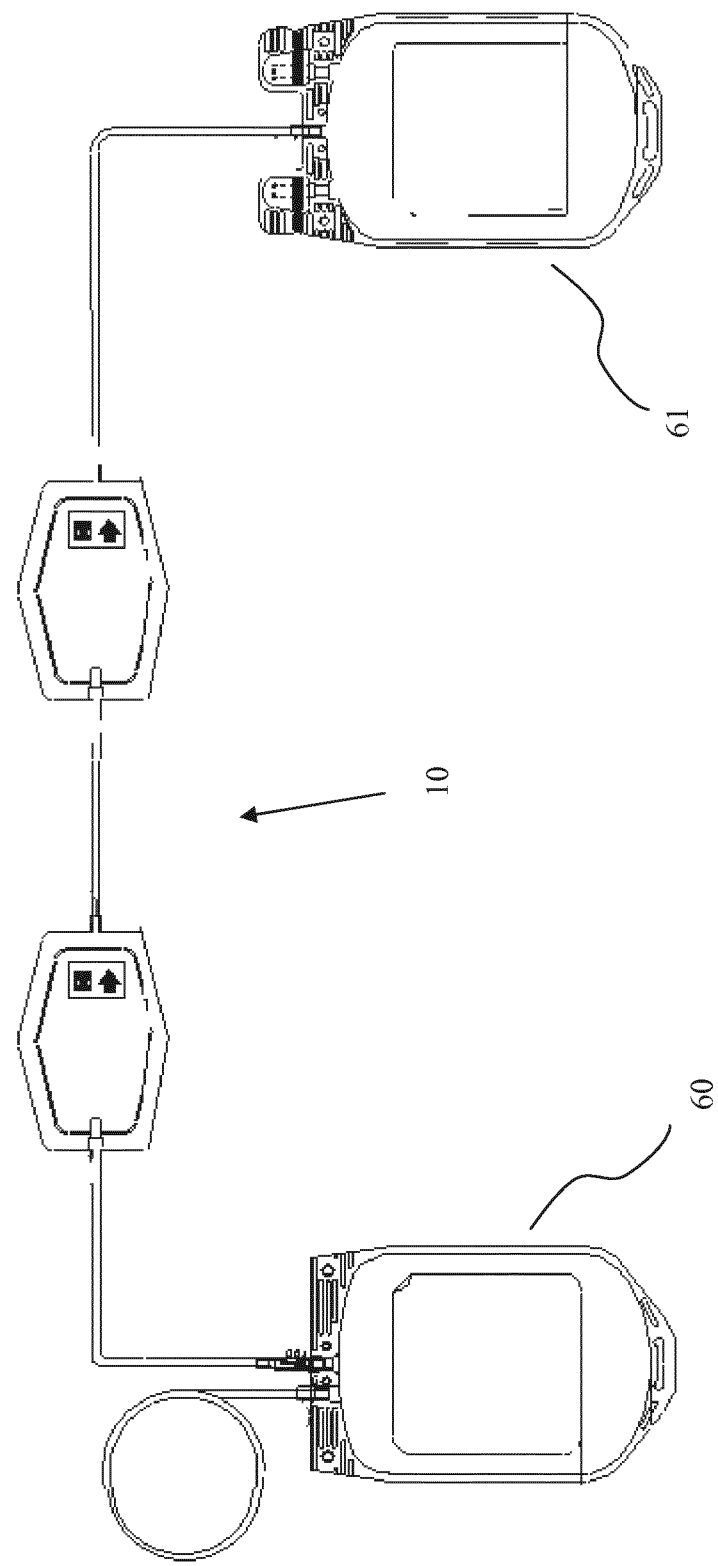

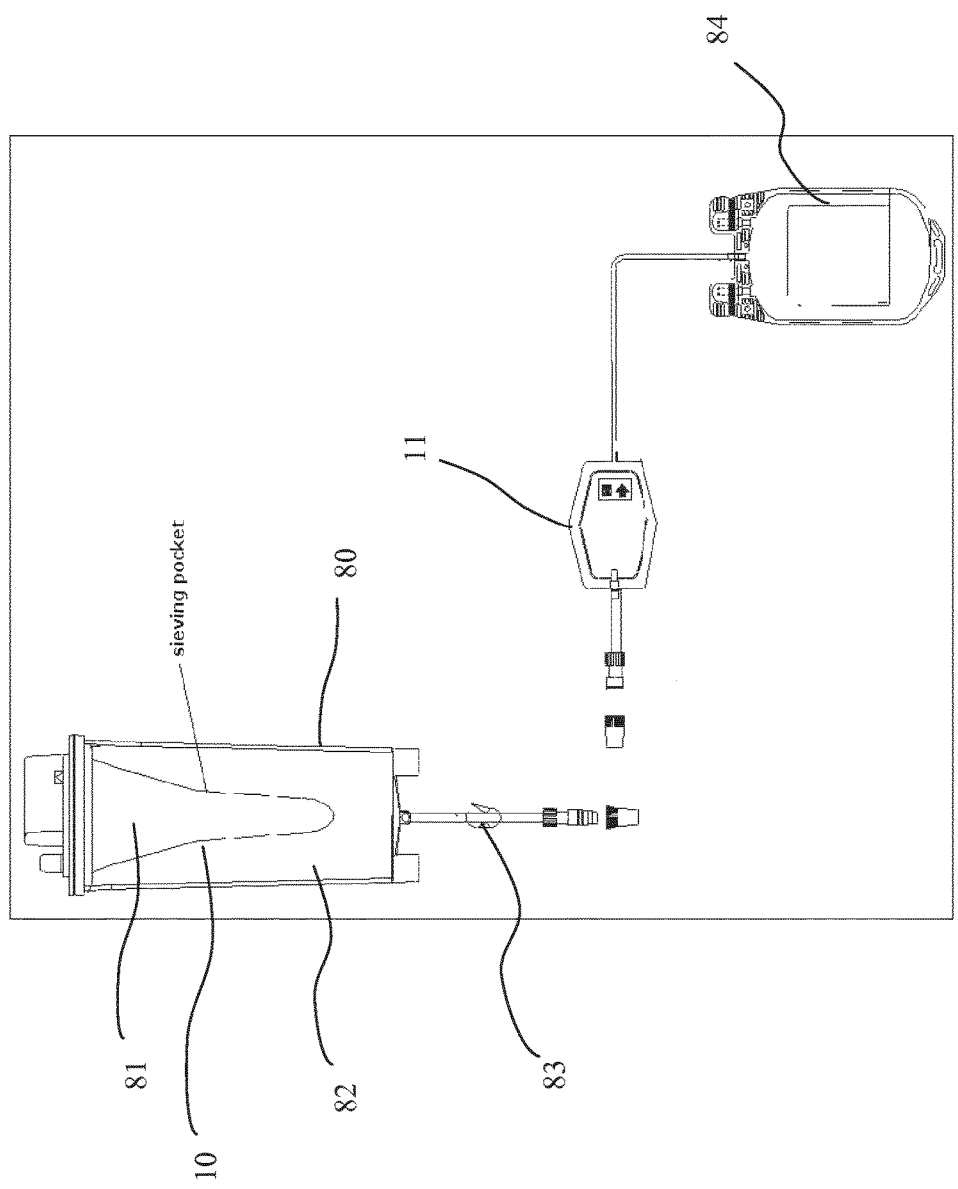

BLOOD FILTER, SYSTEM AND USE OF A BLOOD FILTER OR SYSTEM

TECHNICAL FIELD OF THE INVENTION

The present invention relates to a blood filter, a system comprising a blood filter and the use of a blood filter or system for the removal of substances from whole blood or blood components.

BACKGROUND

Whole blood (WB) comprises three major cellular components, red blood cells (RBCS) and leukocytes (also designated as white blood cells, WBCs) as well as thrombocytes (also designated as platelets, PLTs), which represent cellular fragments derived from precursor cells. A major non-cellular component of the blood is the blood plasma.

Whole blood or blood components may be separated and further processed for a variety of uses, particularly for use as transfusion products.

While WBCs represent an essential part of the body's immune system, the presence of WBCs in a number of products, such as for example transfusion products, is undesirable, because WBCs can cause adverse effects in a patient receiving a blood transfusion, like febrile non-hemolytic reactions, graft-versus-host disease, and immunosuppression. Thus, WBCs are routinely separated from whole blood or blood components for transfusion by filtration.

PLTs are involved in the formation of blood clots, and are therefore often removed from whole blood or blood components, in order to avoid clot formation in a blood product.

Furthermore, it may be desirable to remove other, non-cellular substances from whole blood or blood components, and especially from shed blood (instead of "shed blood" also the term "cell salvage blood" is used).

Commercially available filters for blood filtration and for the depletion of WBCs and/or PLTs from whole blood or blood components are made using membrane technology, fiber technology, or a combination thereof.

Fibers suitable for blood filtration are widely commercially available. Usually, nonwoven fibers produced with different methods such as spunbonding or melt blowing are used in blood filtration applications.

While spunbond fibers typically have a fiber diameter that is at least 20 µm or larger, melt blown fibers may have lower diameters of less than 20 µm. Typical diameters of melt blown fibers are 1 to 3 µm.

The fine melt blown fibers offer the advantage of a high surface area due to their small diameter. Nonwoven melt blown fibers are well suited for the removal of WBCs from whole blood or blood components. The higher surface area of melt blown fibers in comparison to, e.g., spunbond fibers allows for an improved adhesion of WBCs, and thus for a more efficient removal of these cells from the whole blood or blood component to be filtered.

However, a problem that is typically encountered during the filtration of whole blood or blood components is the formation of a so called "gel" or "biofilm". During filtration, this biofilm, which partially consists of activated platelets, plasma factors and cellular micro-aggregates, is successively deposited on the first filtering layers of a blood filter, and thereby causes a successive reduction in filtration flow that eventually can result in the complete blockage of the filter.

In the prior art, blood filters comprising a pre-filter portion in addition to a main filter portion designated, e.g. for the removal of WBCs from whole blood or blood components, have been used to protect the main filter portion from filter blockage. Often, pre-filters are made of spunbond fibers, because these fibers typically have a comparably large diameter of 20 µm or more, and are therefore better suited for pre-filtration applications than the finer melt blown fibers.

However, the pre-filters used in the prior art do not completely avoid the occurrence of reduced filtration flow or even clogging of the main filter portion, because a part of the biofilm is not efficiently entrapped in the pre-filter and thus penetrates into the main filter portion, which usually, due to its structure, e.g. due to a smaller pore size, is much more prone to blockages caused by the deposition of biofilm.

Attempts have been made to select pre-filtering materials with optimized surface chemistry and density, in order to achieve a better adhesion of the biofilm in the pre-filter designed to entrap the biofilm without blocking blood flow. However, this approach has the shortcoming that it results in increased blood loss, and thus loss of desired filtration product, during filtration, caused by the pre-filter structure.

Often, pre-filters are also constructed so as to provide an enlarged surface by means of a reduced fiber size in order to achieve a better distribution of the biofilm on the pre-filter surface. However, a considerable disadvantage to this approach likewise is the consequent higher loss of blood that is caused by the enlarged pre-filter surface.

Consequently there is a need for an improved blood filter for the filtration of whole blood and blood components that is less prone to flow-reduction or clogging of the filter associated with biofilm formation.

SUMMARY OF THE INVENTION

The blood filter according to the invention comprises an inlet, an outlet and at least first fibers disposed between the inlet and the outlet for filtering a fluid being communicated between the inlet and the outlet, wherein each of the first fibers comprises at least one groove extending in the longitudinal direction of the fiber.

A "blood filter" according to the invention is a filter for filtering whole blood, one or more blood components or shed blood for the removal of substances from the blood or blood components, especially for the removal of micro-aggregates, gels, PLTs (platelets), fat, leukocytes, thrombocytes, cellular debris and/or fragments of cells or bones, or a combination thereof.

In particular, the blood filter according to the present invention allows, without being restricted to this use, for an excellent removal of PLTs from whole blood, shed blood and/or blood component to be filtered. Advantageously, the blood filter of the present invention also allows for an improved filtration flow and diminished risk of blood filter blockage combined with an excellent ability to remove substances like WBCs, PLTs, fat, micro-aggregates, gels, cellular debris and/or fragments of cells or combinations thereof from whole blood and/or blood components.

These advantageous properties of the blood filters and systems of the present invention can be attributed to the specific structure of the blood filter that allows to diminish or even to completely avoid the formation and deposition of biofilm on the blood filter during the filtration of whole blood and/or blood components.

Biofilm formation is a phenomenon that is frequently observed during the filtration of whole blood and/or blood components. Biofilm formation results in the deposition of a biofilm on the blood filter, which in turn leads to a reduction of filtration flow and eventually can lead to the complete clogging of the blood filter.

Through scanning electron microscope (SEM) and biochemical studies conducted on blocked blood filters, the inventors have found that biofilm formation, which results in a diminished filtration flow and which ultimately can result in filter blockage, is triggered by PLTs. When contacting the filter, PLTs become adherent to e.g., nonwoven fibers of the filter, thus creating bridges between one another and between fibers of the filter. When the number of bridges formed by the PLTs increases, other cells, for example WBCs, resting PLT, RBCs, cellular fragments and non-cellular matter such as proteins or fat accumulate, eventually resulting in the formation of a macroscopically apparent biofilm.

The inventors have now found that the adhesion of PLTs preferably occurs at knots of nonwoven fibers, or where ribbons of twisted nonwoven fiber, the location of nonwoven fibers in bundles or other structures bring two nonwoven fibers in close contact with each other. These are also the locations where the formation of the biofilm starts. Generally spoken, a location of nonwoven fibers close to each other may result in an enhanced interaction time between the nonwoven fibers and PLTs, and may thus act as a trigger of biofilm formation.

Based on the above-mentioned observations, but without wishing to be bound by theory, the inventors have found that approaches aiming to improve the blood filtration performance by reducing the diameter of nonwoven fibers, which is often done to increase the relative surface of the fibers, are only partially useful.

On the one hand, when using nonwoven fibers with smaller diameters, the surface area of the filter is increased and the removal of WBCs from whole blood or blood components by the filter may therefore be enhanced. This allows for efficient removal of WBCs with filters made of, e.g., melt blown nonwoven fibers.

However, WBCs are comparably large cells, with a diameter of approximately 10 µm to 20 µm, depending on the subtype of WBC. On the other hand, resting PLTs are much smaller, with an average diameter of 2 µm to 3 µm, although it increases by cell activation. Thus, when reducing the fiber diameter, adhesion of the PLTs to the fibers seems to become more difficult. As a consequence, in filters with a low fiber diameter of below 20 µm, PLTs are no longer uniformly distributed on the filter surface. Instead, knots, bundles, ribbons and other fiber structures where the distance between two nonwoven fibers is less than the average diameter of a PLT become more important as adhesion sites of PLTs. PLTs tend to accumulate at these structures, which thus act as trigger point of biofilm formation.

Hence, with decreasing fiber diameter, the risk of a reduction in filtration flow and of blood filter blockage increases, while the overall adhesion of PLTs to the fibers is poor. Consequently, also the removal of PLTs from whole blood or blood components is diminished, albeit the surface area of the filter increases with reduced fibre size.

The inventors have now found that surprisingly, when fibers with at least one groove are used in the blood filter, the removal of PLTs from whole blood or blood components can be improved, while reduction in filtration flow and filter clogging are significantly reduced. Such grooves, due to their shape, seem to improve the platelet adhesion, even if the diameter of the fiber is rather small, especially below 20 µm. Furthermore, such grooves also seem to have a positive effect even if the fibers have a diameter which is much larger, especially about or above 20 µm.

Furthermore, it is preferred, that the surface of the fibers, in particular in the region of the grooves, is smooth. Such a smooth surface can be obtained, for example, by extruding the shaped fibers. An extrusion of the fibers also has advantages in regard to biocompatibility, especially in comparison to laser-ablation procedure which might leave traces within the filtering matrix, like chemical byproducts due to degradation and/or particles of the ablated thermoplastic polymer. Furthermore, chemical byproducts type and toxicity issues can arise by laser ablation, depending on the material used. This risk is reduced or even absent with the extrusion shaped-fibers approach. In addition, a smooth surface does only slightly induce or does not induce at all shear stress on, for example, the cellular membrane of eritrocytes (hemoglobin carriers) passing through such a filtering material. A high shear stress might increase the risk of hemolysis. Besides extrusion, of course other processes for obtaining fibers with a smooth surface could be used.

According to a preferred embodiment, the surface roughness of the fibers Ra (average roughness) is Ra equal or less than 0.1 µm, preferably Ra equal or less than 0.03 µm, most preferably Ra equal or less than 0.01 µm The invention is not restricted to the use for removing leucocytes (WBC) and/or platelets (PLT's) from whole blood or blood components. The blood filter may be also used, for example, for filtering shed blood for the removal of bone fragments, clots, activated platelets, micelles, macro-aggregates and/or other substances.

According to a preferred embodiment of the invention, the first fibers have a lobate shape, preferably a trilobate shape. Especially the trilobate shape seems to be very effective for providing a good filtration flow and reducing filter clogging. However, other fiber shapes could be also used, for example T-shaped, V-shaped or kidney-shaped fibers, fibers with tetralobate or pentralobate shapes, or fibers with at least one groove with a partially concave shape in general. Of course, a mixture of different fiber shapes is also possible.

According to another preferred embodiment of the invention, the groove of first fibers has a length of at least 10 µm, preferably of at least of 100 µm. This provides for a sufficient surface area of the grooves which can interact with different substances in the blood or blood component, especially with platelets.

According to another preferred embodiment of the invention, the diameter of the first fibers is in the range of 5 to 50 µm. According to this invention, the diameter corresponds to the diameter of the smallest circle which still encloses the cross section of the fiber, as shown in FIG. 2. For pre-filtration purposes, fibers are preferably in the range 20 to 50 µm, more preferably in the range 20 to 40 µm, preferably with decreasing diameter for deeper stages nearer to filtration stages. For filtration stages, fibers are preferably below 20 µm, more preferably below 5 µm. Especially such diameters could be used, which the person skilled in the art would usually use for their equivalent round fibers.

According to another preferred embodiment of the invention, the first fibers are spunbond fibers and/or meltblown fibers. Furthermore, the first fibers may be monocomponent, bicomponent or multicomponent fibers, including "island in the sea"-fibers. The first fibers may consist of one polymer or a blend of polymer. Suitable materials for fibers are, for example, polyethylene, polypropylene, polybutylene, polymethylpentene, polyethylene terephthalate, polytrimethylene terephthalate, polybutylene terephthalate, poly(butylene terephthalate-co-polyalkylene glycol terephthalate), nylon 6,6, nylon 6,9, nylon 6/12, nylon 11, nylon 12, cellulose acetate, cellulose acetate propionate, or a combination thereof.

According to another preferred embodiment of the invention, the filter comprises at least one layer of nonwoven fibers, wherein at least a part of the fibers of the layer are first fibers. The fibers of layer are bonded together by, for example, chemical, mechanical, heat or solvent treatment. For example, in a melt blown process fiber bonding occurs at the lay down due to entanglement and adhesion of the fibers. The combination of fiber entanglement and fiber-to-fiber bonding generally produce enough web cohesion so that the web can be readily used without further bonding. However, additional bonding and finishing processes may further be applied. In addition or as an alternative, the filter may comprise at least one layer of woven fibers, wherein at least a part of the fibers of the layer are first fibers.

According to another preferred embodiment of the invention, the at least one layer comprises at least 20%, preferably at least 50% and most preferably at least 80% weight percent of first fibers. Ideally, the layer may consist of 100% first fibers. Having a greater share of first fibers in the layer improves filtration flow rate and reduces filter clogging. However, a mixture with other types of fibers (i.e. second fibers) is possible, especially if the layer should comprise additional functions.

According to another preferred embodiment of the invention, the blood filter comprises at least a first set and second set of filter layers, the at least first and second set arranged such that fluid flowing from the inlet to the outlet passes the first set before passing the second set, each set comprising at least one filter layer, wherein the two adjacent filter layers of two subsequent sets are different in their properties. The difference between the two adjacent filter layers may be in shape, porosity, CWST ("critical wetting surface tension"), basis weight, diameter, material and/or chemical or mechanical surface properties. This allows for defining different filtration stages for the blood filter. The first set may define a pre-filtration stage, whereas the second set and, if present, subsequent sets may define one or more selective filtration stages. Preferably, the blood filter comprises 2 to 7 sets, more preferably 2 to 5. The number of sets depends upon complexity of filtration and required porosity gradient (RCC filters have in general fewer sets than WB's). A set preferably consists of one or more identical layers. Stacking identical layers allows for obtaining an appropriate overall thickness while keeping uniform properties. A set may comprise, for example, 1 to 20 layers, preferably 1 to 10 layers and even more preferably 1 to 5 layers.

According to another preferred embodiment of the invention, the first set comprises at least one layer with first fibers, the first fibers having a groove with a depth (measured from the external circle, as from FIG. 2) in the range of 5 µm to 15 µm, more preferably in the range 7 µm to 10 µm. Of course the maximal possible depth of the groove is restricted by the fiber diameter. In this case, the first set would be especially adapted for pre-filtration purposes, especially for reducing the amount of micro-aggregates, gels, fat, cellular debris and/or fragments of cells. In such a case, fibers with a larger diameter would be used, usually with a diameter about or above 20 µm, and the fiber layer usually would have a higher porosity than the layers of the subsequent set or sets.

According to another preferred embodiment of the invention, the second set comprises at least one layer with first fibers, the first fibers having a groove with a depth in the range of 0.2 µm to 5 µm. In this case, the second set would be especially adapted for selective filtration purposes, preferably for reducing the amount of WBC, while also supporting a good flow rate and reducing clogging. In such a case, fibers with a smaller diameter would be used, usually with a diameter below 20 µm, and the fiber layer usually would have a smaller porosity than the layers of the first set.

According to another preferred embodiment of the invention, the first set and the second set comprise at least one layer comprising first fibers, wherein the diameter of first fibers in the first set is greater than the diameter of first fibers in the second set. This allows, for example, to create a porosity gradient which can provide for effective pre-filtering and/or distribution of entrapped substances, reducing clogging and reduction of flow rate.

According to another preferred embodiment of the invention, the filter comprises at least one soft housing and/or a hard housing accommodating the at least first fibers. A hard housing, which is rigid, offers mechanical stability. A soft housing, which is flexible, has advantages in regard to production costs and volume loss. Inside the at least one housing, if the blood filter comprises more than one layer or more than one set, the layers and sets preferably are under at least slight compression so that gaps between adjacent layers, which might reduce the flow rate, are diminished or prevented. Alternatively or in addition, adjacent filter layers may be, at least partially, bonded together, for example by thermal bonding.

According to another preferred embodiment of the invention, the first set and the second set are arranged in a single housing. Alternatively, the first set and the second set are arranged in different housings, the housings being in fluid communication.

A system for processing whole blood, shed blood or at least one blood components, includes, according to the invention, at least one blood filter, wherein the filter is arranged between a first reservoir and a second reservoir. The system may be a blood bag system, the first reservoir and the second reservoir being blood bags, the system especially being adapted for filtering whole blood or blood components. The system may be a system for processing shed blood, wherein the first and second reservoir are being part of a rigid or flexible container.

According to the invention, the system or the blood filter can be used for the removal of substances from whole blood or blood components, wherein the blood components are selected from the group comprising shed blood, whole blood, red cell concentrate, platelet rich plasma, platelet concentrate and plasma.

BRIEF DESCRIPTIONS OF THE DRAWINGS

Figure 5A:
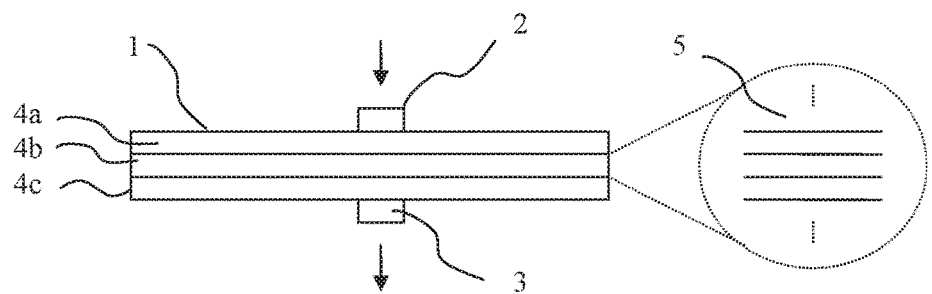
Figure 5B:
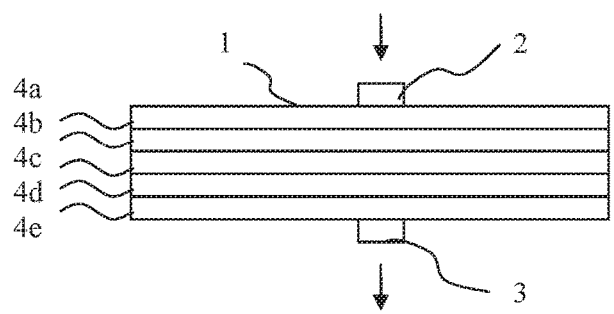
Figure 5C:
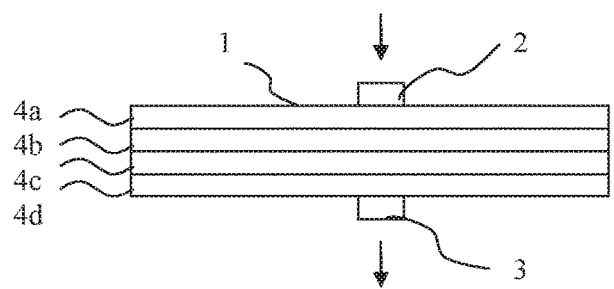

FIGS. 5A, 5B and 5C schematically depict exemplary blood filters according to the present invention. The Figures are not drawn to scale.

Figure 6A:
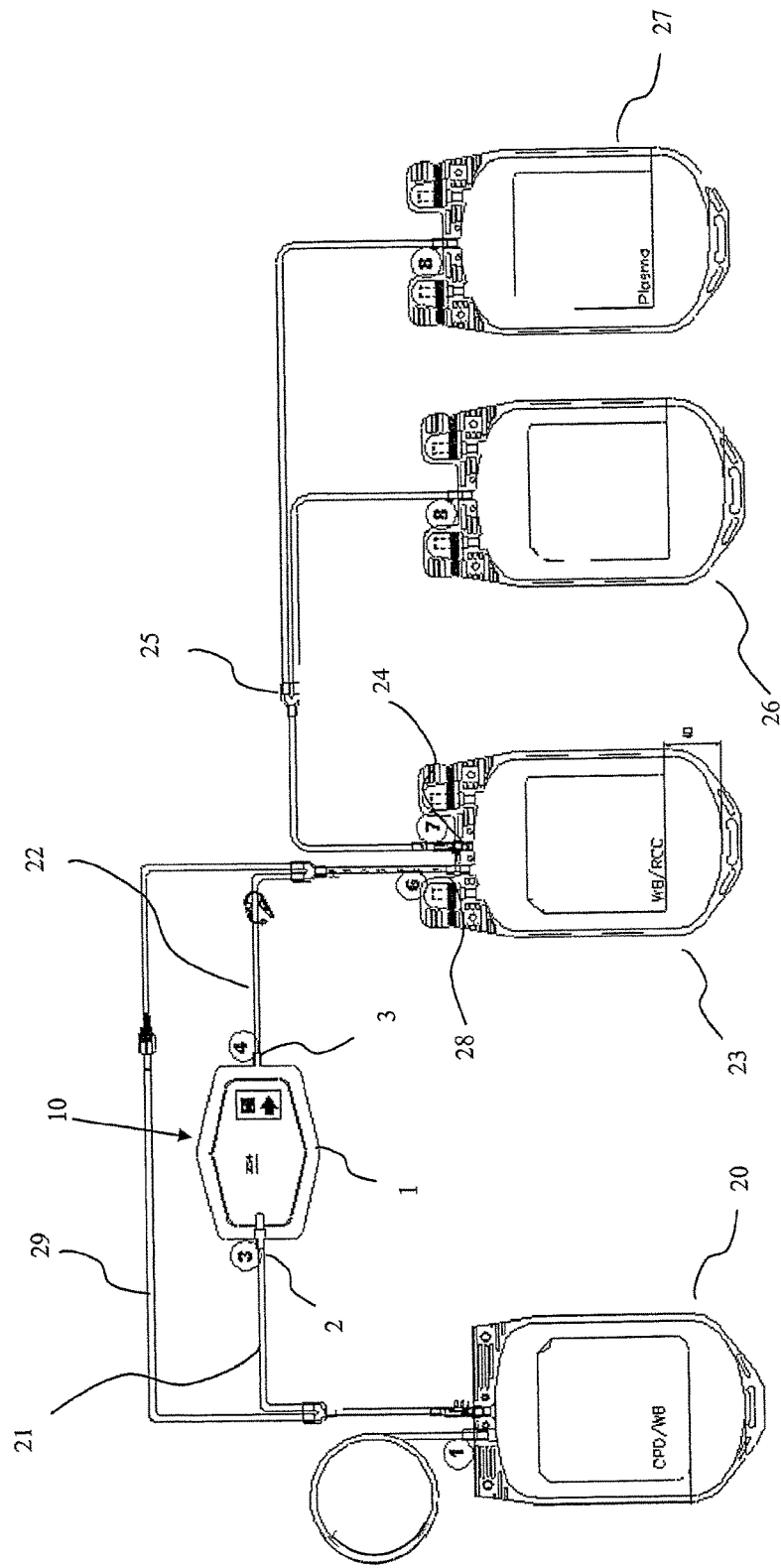
Figure 6B:
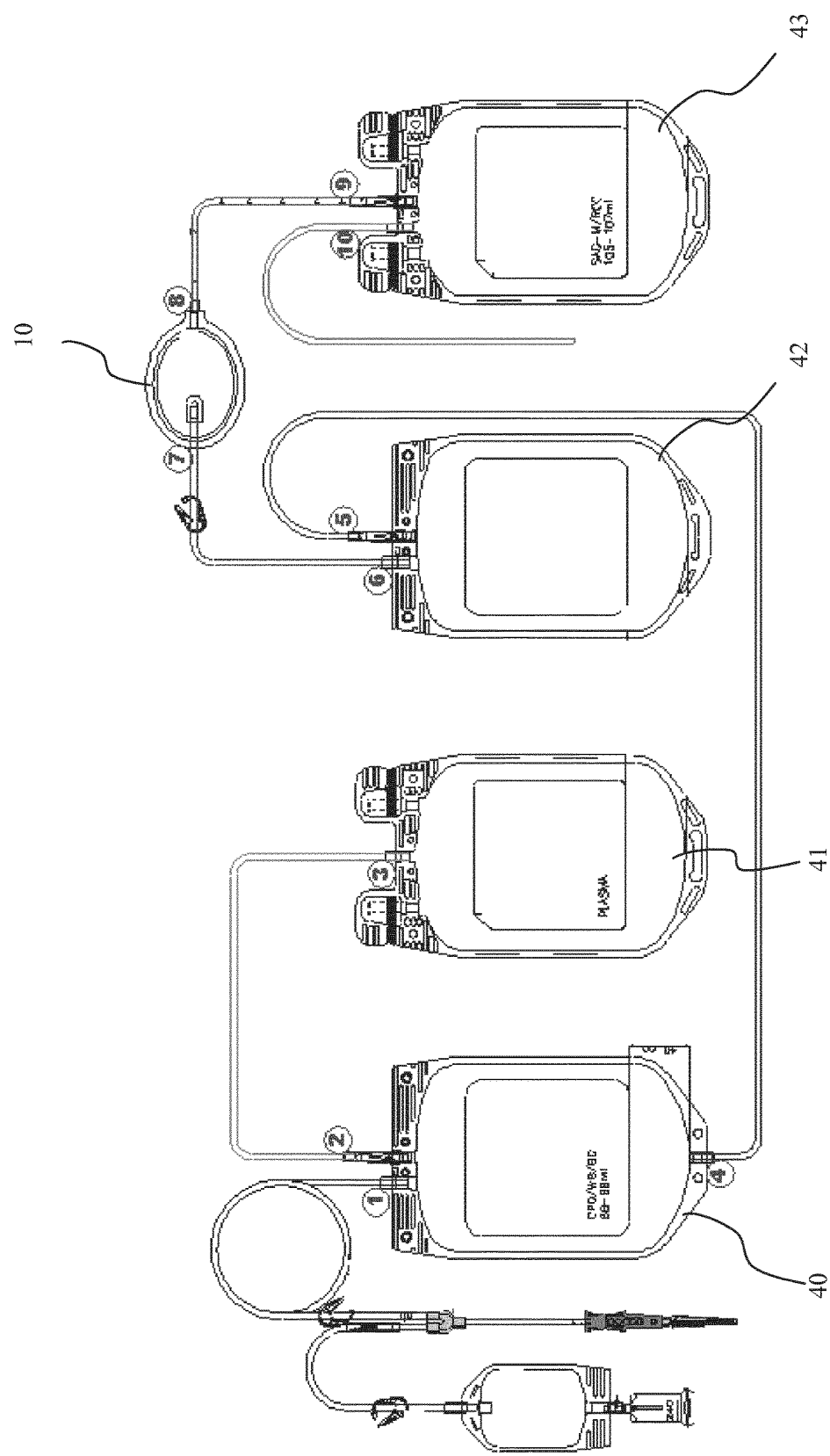

FIGS. 6A, 6B and 6C schematically depict exemplary systems for the removal of substances from whole blood or blood components according to the present invention. The Figures are not drawn to scale.

FIG. 7 depicts an exemplary system for the removal of macro aggregates and solid fats from shed blood upstream the primary filtration.

EMBODIMENTS OF THE INVENTION

FIG. 1 shows scanning electron microscope (SEM) pictures of the first layer of a whole prior art blood filter (A, B) and a subsequent layer of the same whole blood filter (C, D) at two different magnifications. The SEM pictures of FIGS. 1 A and C are presented at a magnification of 1500, while the SEM pictures of FIGS. 1 B and D are presented at a magnification of 800. The SEM pictures show the biofilm deposition occurring in filter layers made of prior art melt blown fibers with a cylindrical cross section.

FIGS. 2A to 2I show several scanning electron microscope (SEM) pictures of the cross sections of first fibers, in this case PET spunbond trilobate fibers.

Figure 1A:
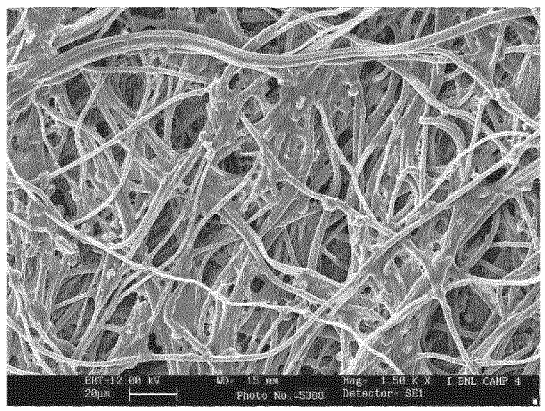
FIG. 1 shows scanning electron microscope (SEM) pictures of the first layer of a whole prior art blood filter (A, B) and a subsequent layer of the same whole blood filter (C, D) at two different magnifications.
Figure 1B:
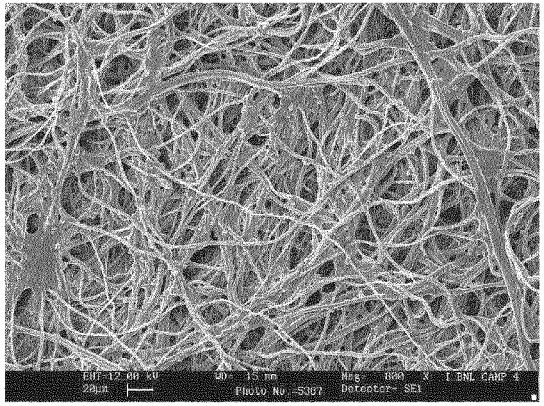
Figure 1C:
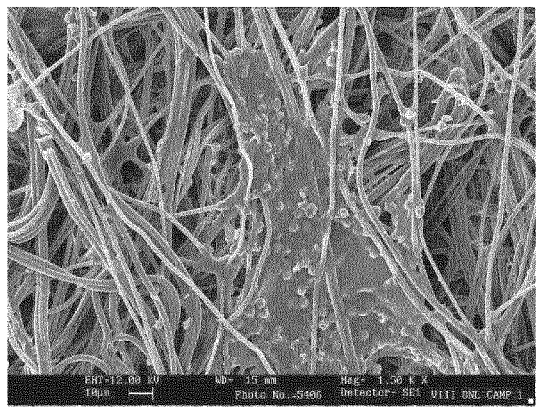
Figure 1D:
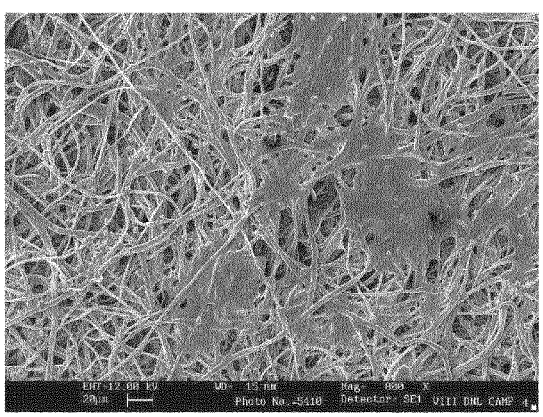
Figure 2A:
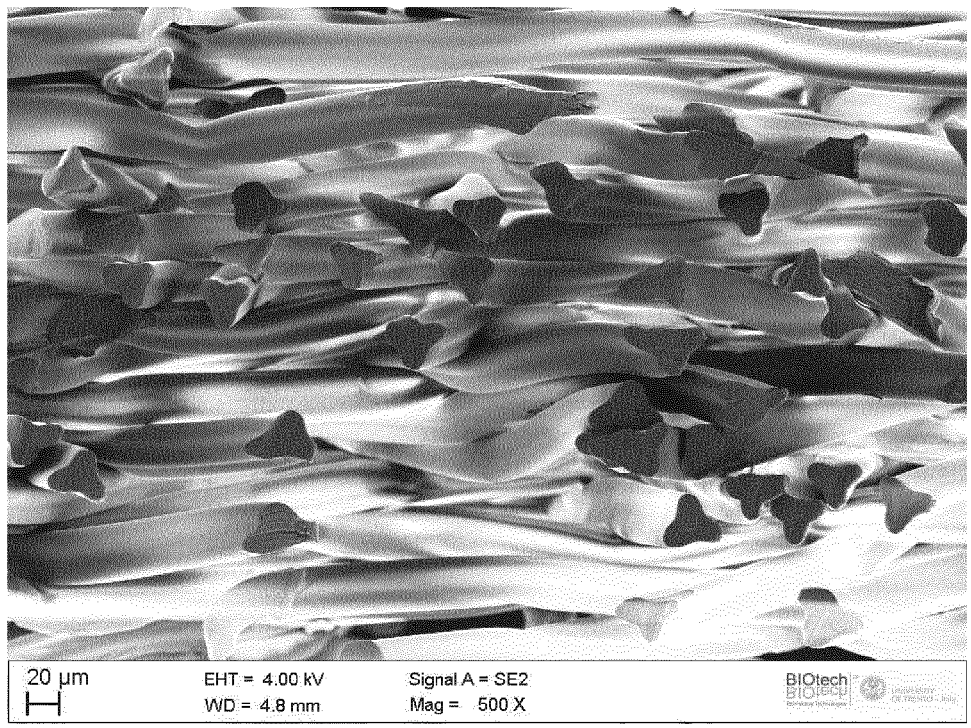
FIGS. 2A-2I show several SEM pictures of the cross sections of PET spunbond trilobate fibers.
Figure 2B:
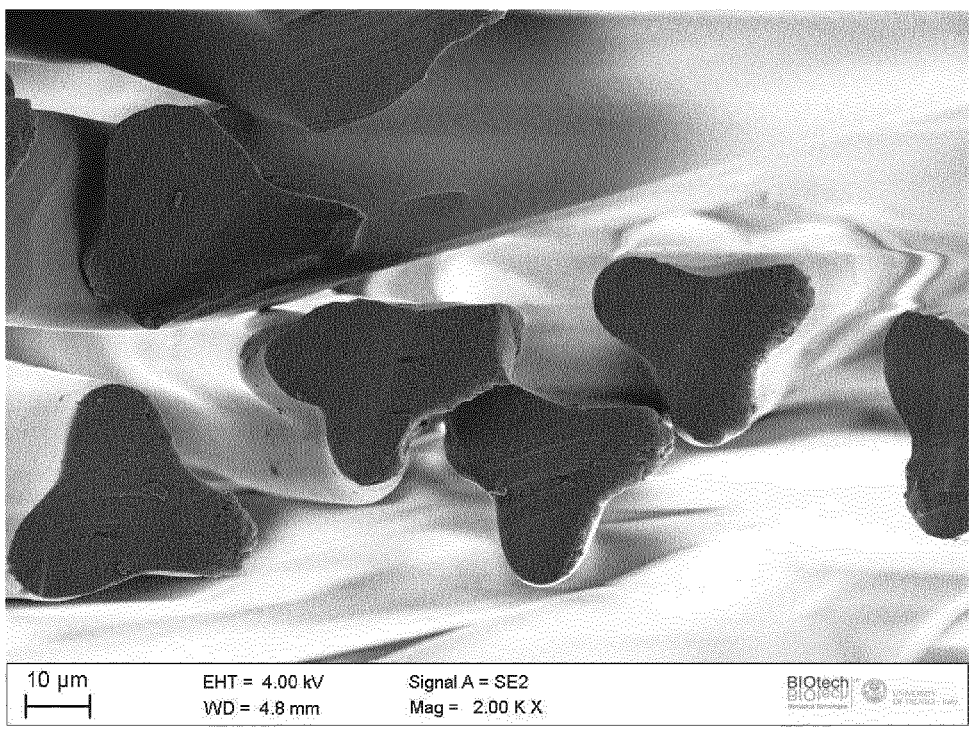
Figure 2C:
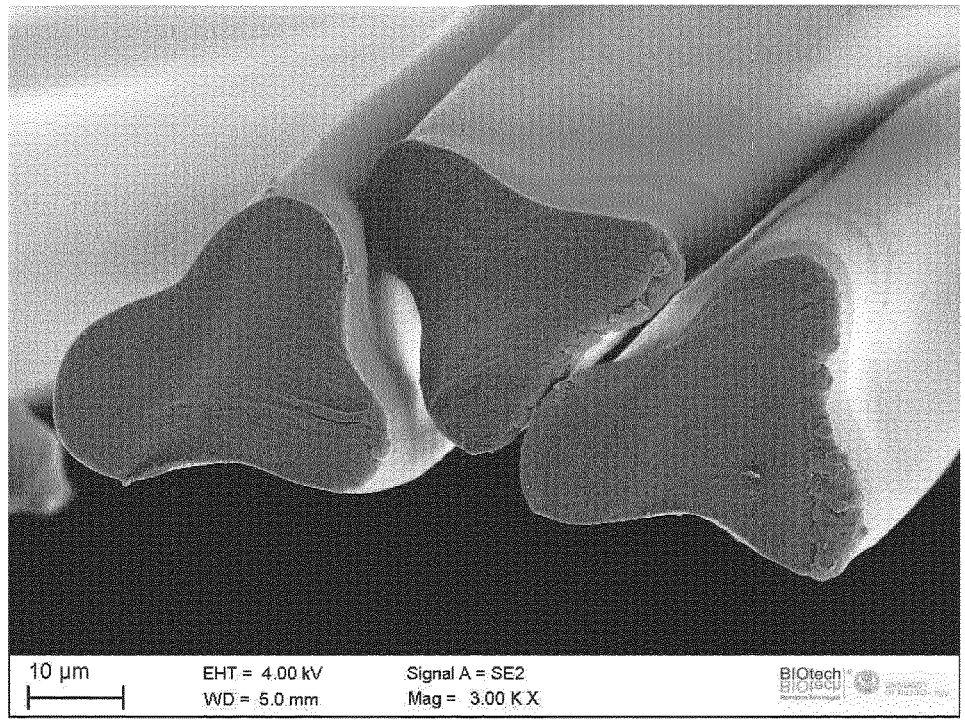
Figure 2D:
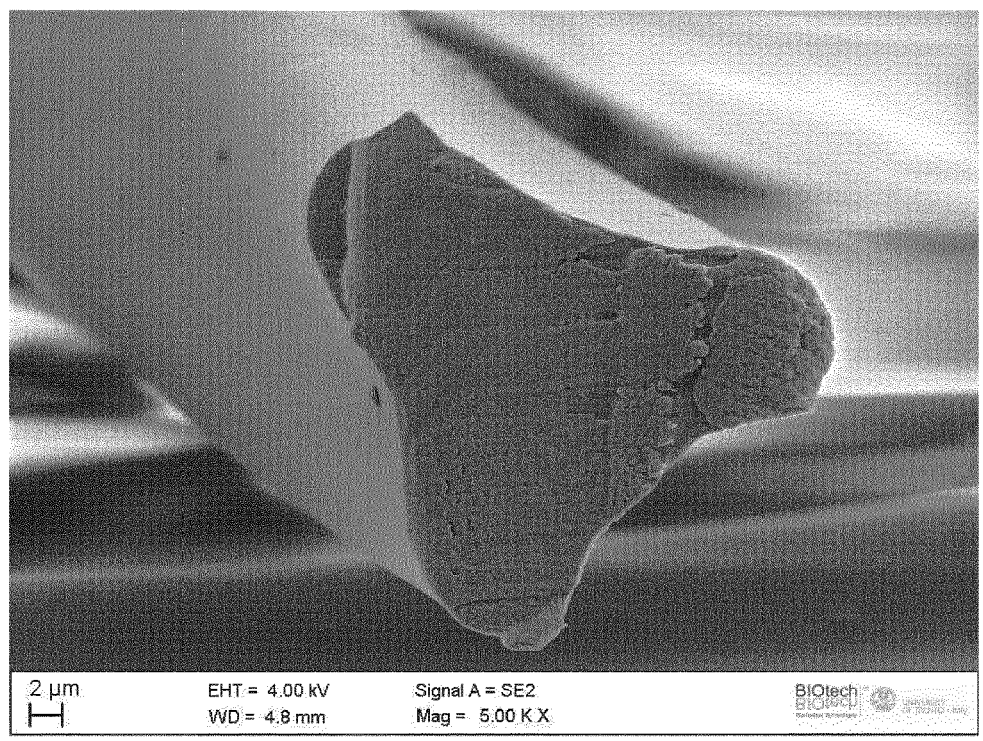
Figure 2E:
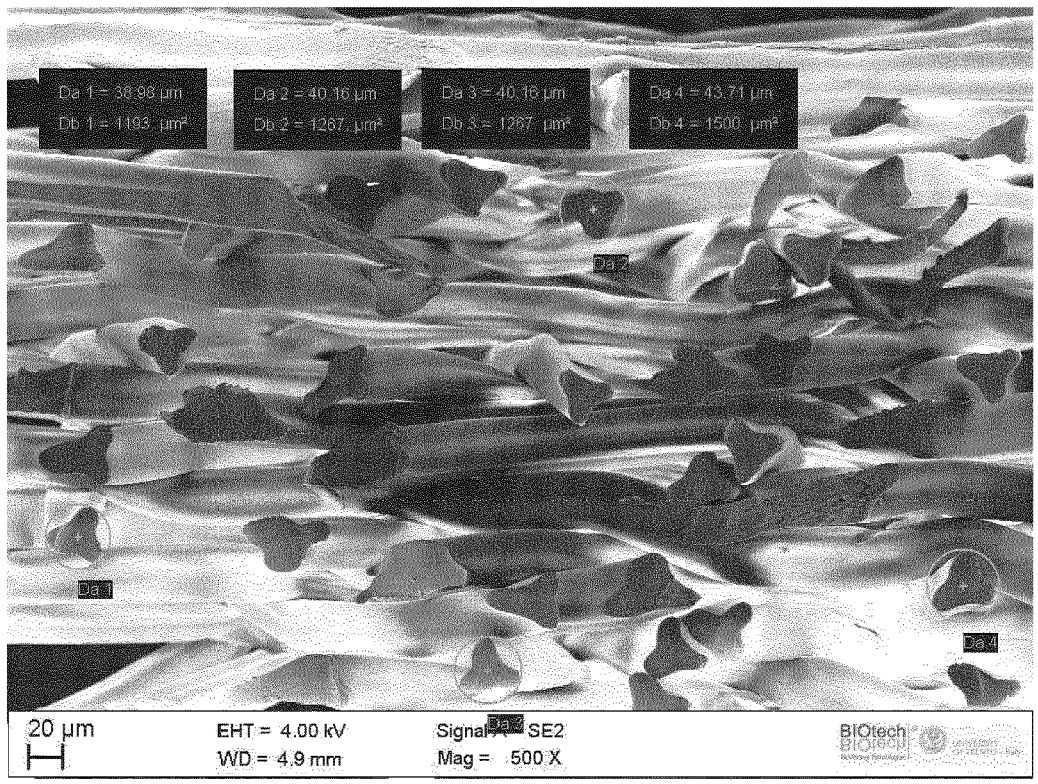
Figure 2F:
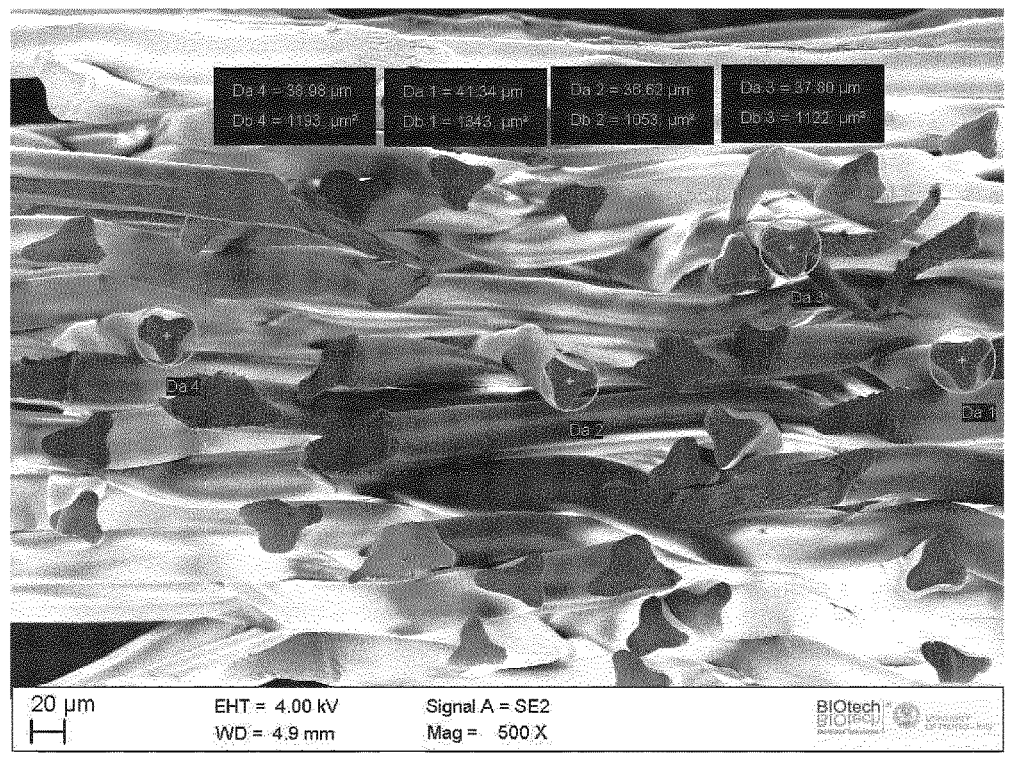
Figure 2G:
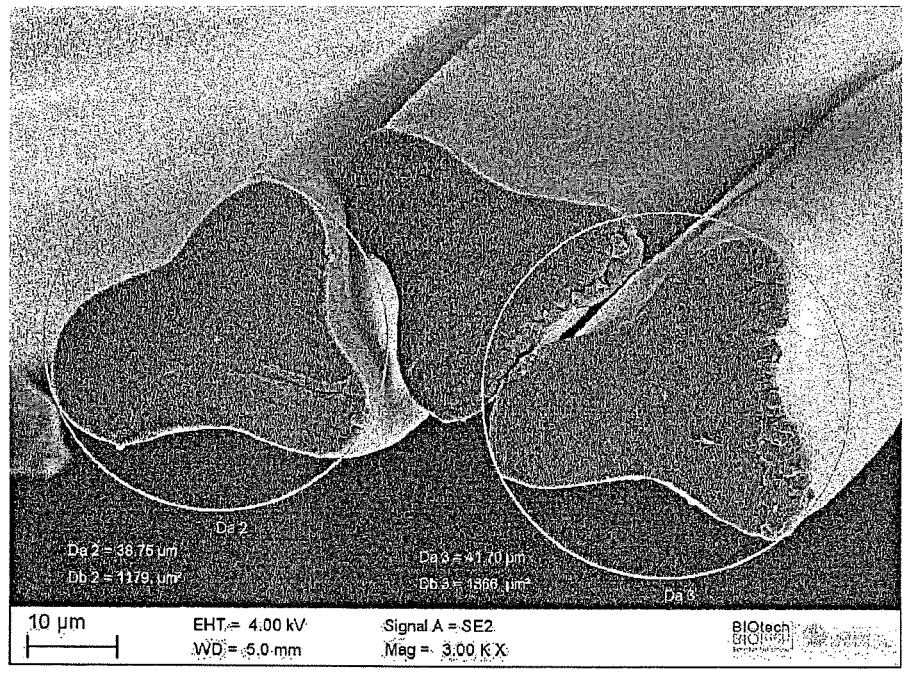
Figure 2H:
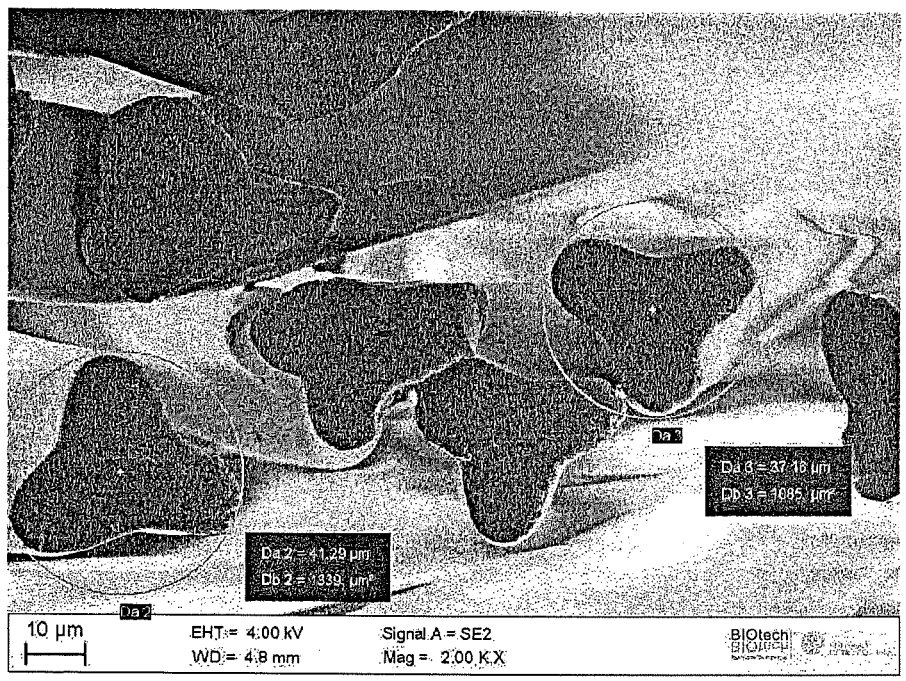
Figure 2I:
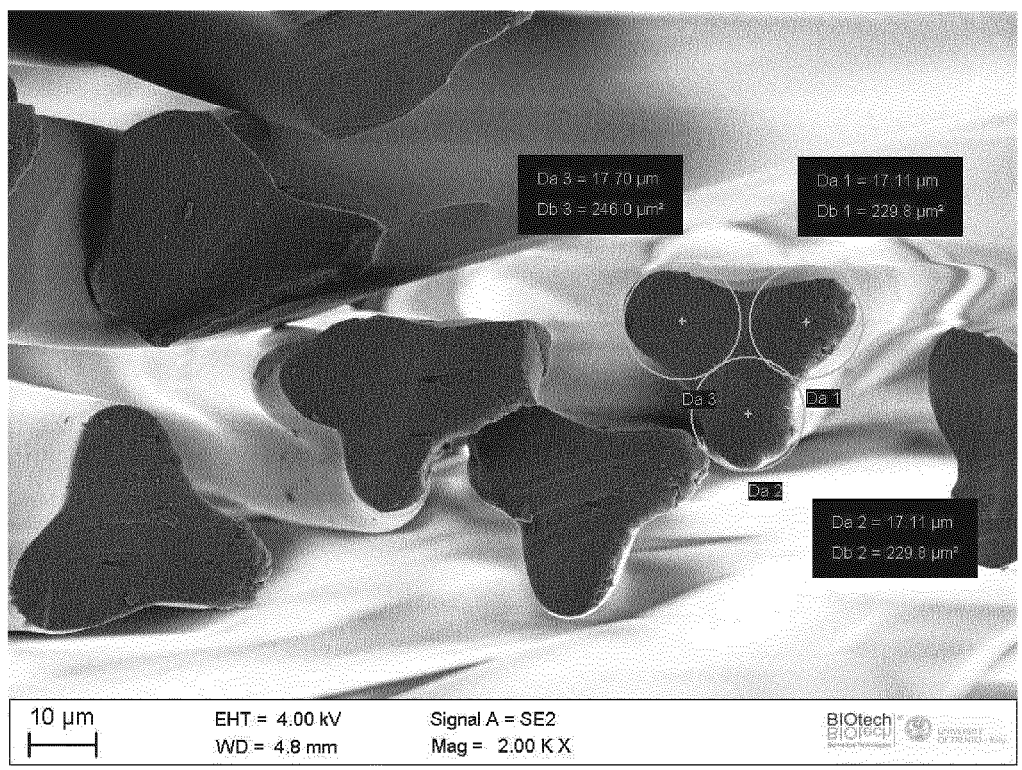
Figure 3A:
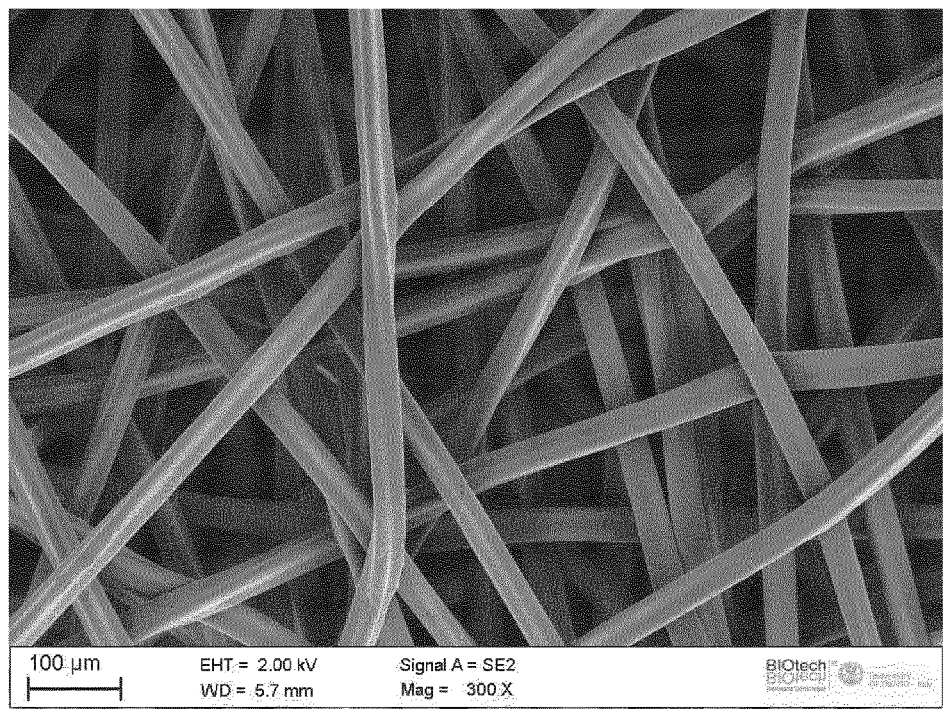
FIGS. 3A-3E show several scanning electron microscope pictures of a layer of trilobate fibers.
Figure 3B:
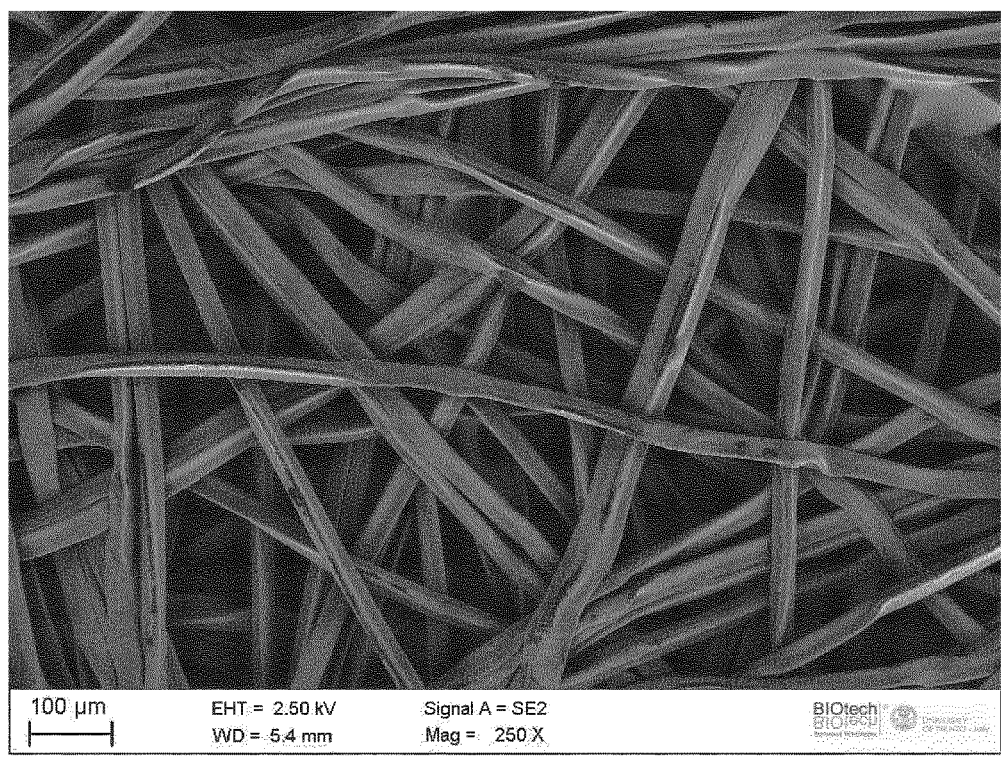
Figure 3C:
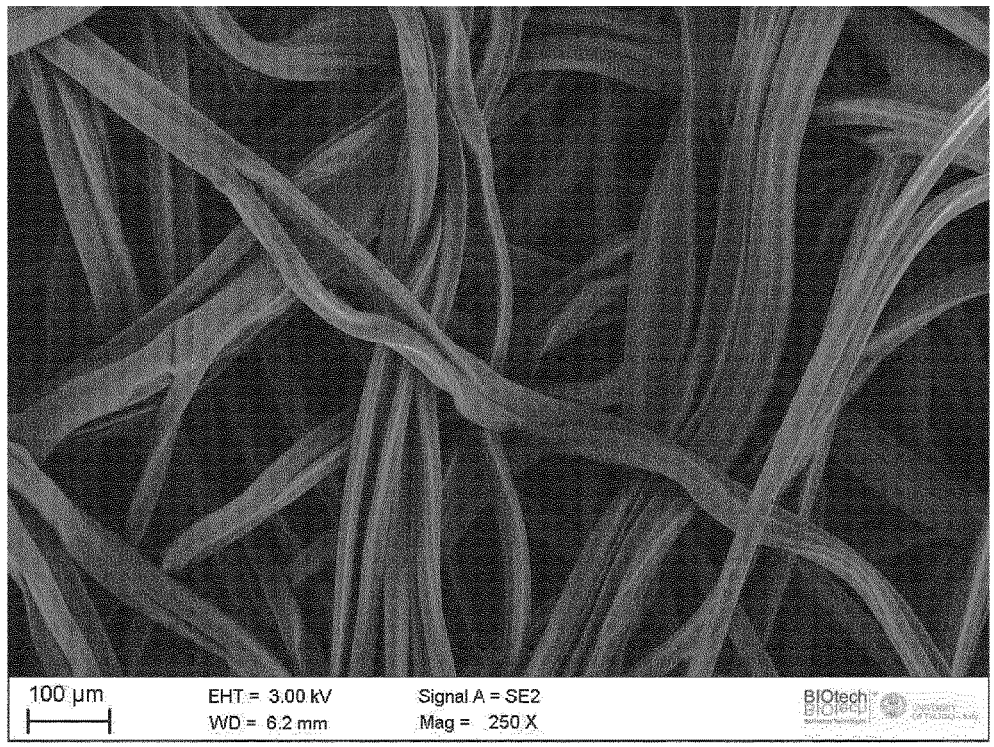
Figure 3D:
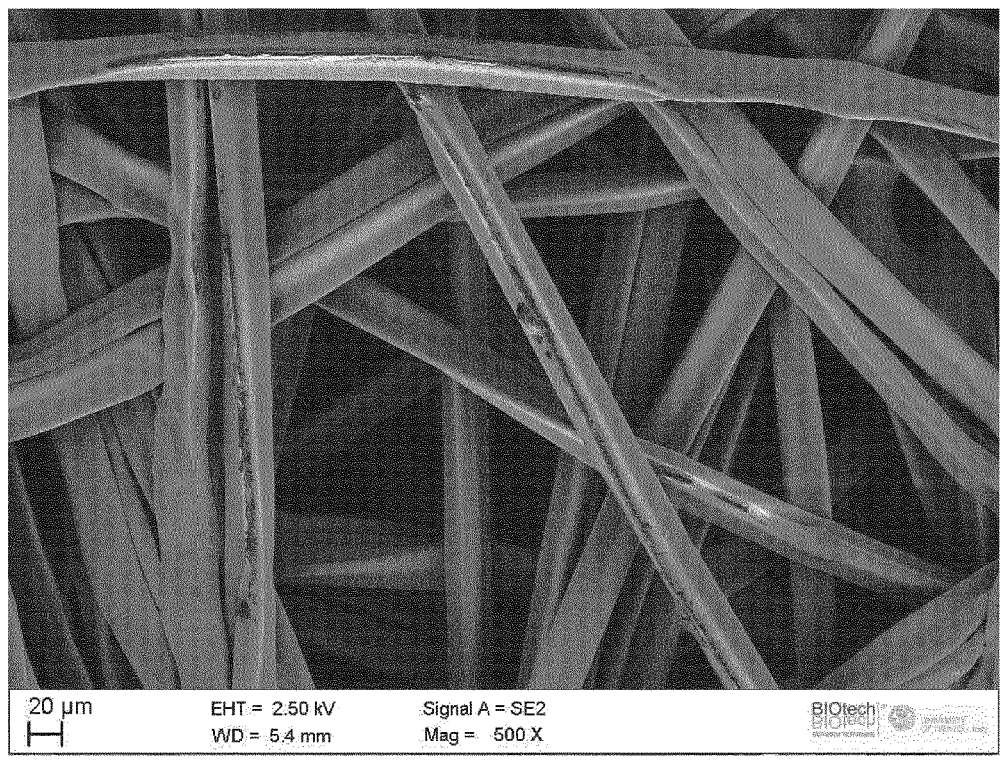
Figure 3E:
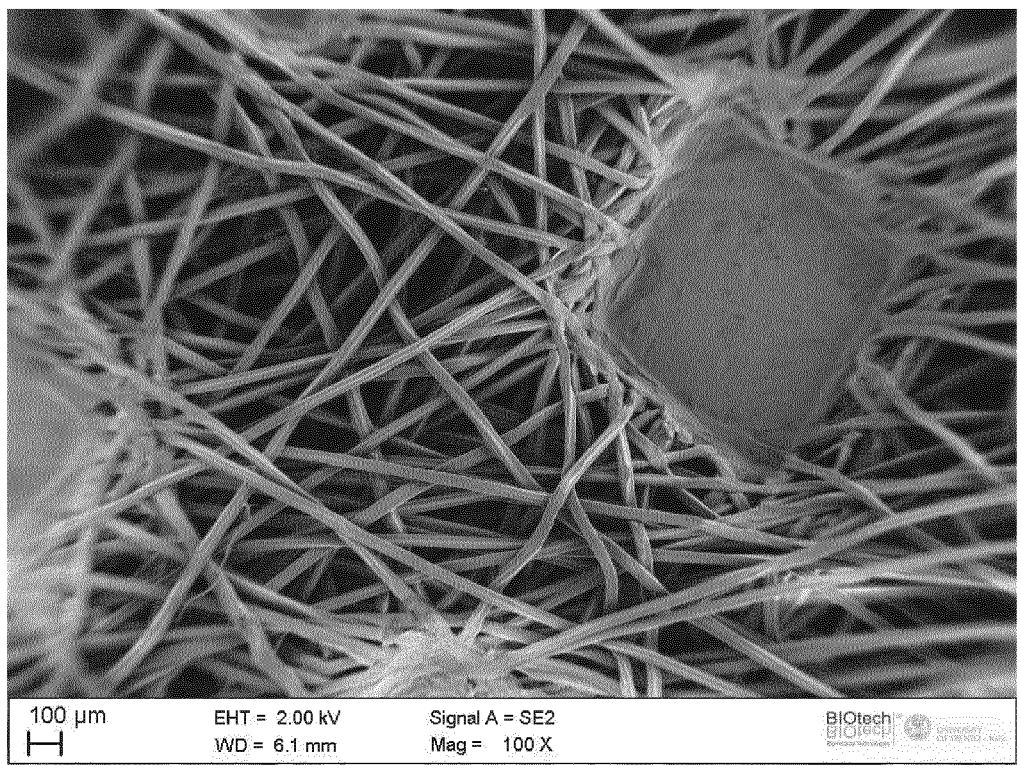
Figure 4A:
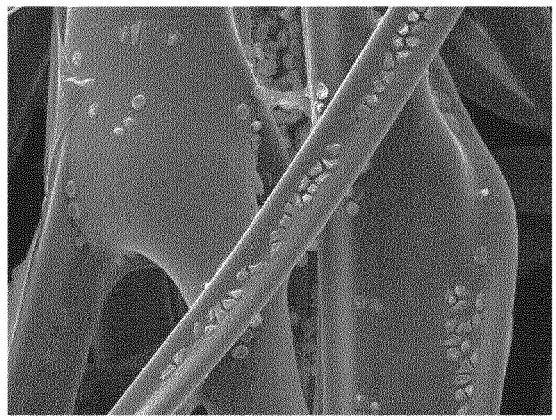
FIGS. 4A-4D show SEM pictures of spunbond trilobate fibers and the preferred adhesion sites of cells.
Figure 4B:
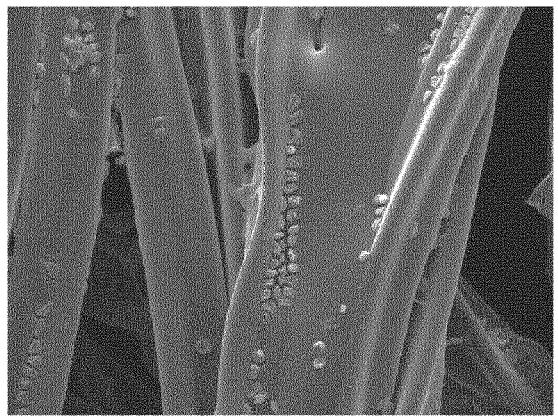
Figure 4C:
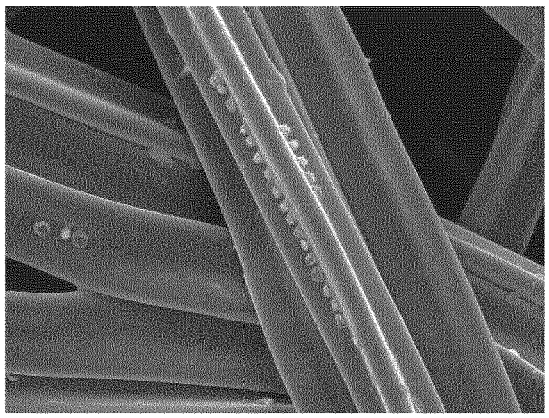
Figure 4D:
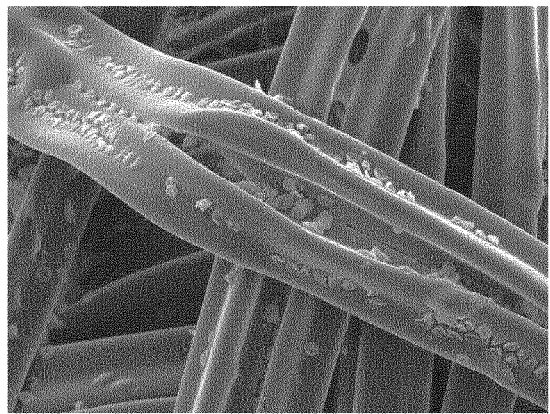

FIGS. 3A to 3E show several scanning electron microscope pictures of a layer of trilobate fibers. The last FIG. 3E shows a point bond.

FIGS. 4A to 4D show SEM pictures of spunbond trilobate fibers and the preferred adhesion sites of cells. It can be clearly seen that cells preferably adhere to the fibers at the surface of the grooves formed by the special geometry of the trilobate fibers. The inventors believe that such grooves of the fibers, which are not restricted to the trilobate shape, contribute to an improved removal especially of platelets, therefore providing for a good flow rate and the reduction of clogging of the inventive blood filter when filtering whole blood, salvage blood or blood components.

In the following, experiments are given which demonstrates the effect of the blood filter comprising first fibers.

Experiment A

A down-scaled (1:10) blood filter of the prior art, comprising a pre-filter portion consisting of one layer of spunbond cylindrical fibers was compared to three different down-scaled (1:10) blood filters according to the present invention. All blood filters tested comprised an identical main filter portion (coated meltblown PBT (Polybutylenterephthalat), 50 g/m$^2$, 2 µm), but differed in the pre-filter portion.

Whole blood obtained from a human donor was stored at 4° C. over night (for 14 hours). When blood that has been stored under these conditions is filtered, the formation of biofilm is especially pronounced with blood filters of the prior art.

In a first step, 40 ml of the blood were applied to each of the pre-filter portions and filtration was performed by application of gravity. The control (C) consisted of blood that had not been subjected to a pre-filtration step.

Then, in a second step, the pre-filtered blood was applied on a main filter portion, consisting of one set of 10 layers of melt blown cylindrical fibers with a fiber diameter of 1 µm to 3 µm. The filtration time and the number of filter blockages were recorded.

The results are depicted in Table I:

| Blood filter | Step I (pre-filter portion) | Step II (main filter portion) | Filtration time [min]$^1$ | Blockages |
|---|---|---|---|---|
| Only main filter portion | C* | 10 layers of mb cylindrical fibers | 23 | 12/20 |
| Prior art | 1 layer of sb** cylindrical fibers: Cylindrical, 100% PET thermal point bonded, ca. 16 µm, 100 g/m$^2$ | 10 layers of mb cylindrical fibers | 14 | 3/20 |
| Blood filter 1 | 1 layer of crimped sb trilobate fibers composition: 100% PET, flat bonded, ca. 40 µm, 100 g/m$^2$, 2 layers | 10 layers of mb cylindrical fibers | 12 | 1/20 |
| Blood filter 2 | 1 layer of crimped sb trilobate fibers composition: 100% PET, flat bonded, ca. 40 µm, 80 g/m$^2$, 3 layers | 10 layers of mb cylindrical fibers | 11 | 1/20 |
| Blood filter 3 | 1 layer of crimped sb trilobate fibers composition: 100% PET, flat bonded, ca. 40 µm, 65 g/m$^2$, 4 layers | 10 layers of mb cylindrical fibers | 8 | 0/20 |

*C, control, no pre-filtration in step I;
**sb, spunbond;
***mb, melt blown;
$^1$median calculated on "n" values excluding blocked filters.

The results depicted in Table I clearly show that blood filters of the present invention are highly efficient in preventing filter blockage. In addition, a decrease of the filtration time was observed. A significantly reduced formation of biofilm was observed with the blood filters of the present invention when compared to the prior art blood filter or to the control.

Experiment B

In a second experiment, the removal of PLTs and WBCs was compared between a down-scaled (1:10) blood filter of the present invention and a prior art down-scaled (1:10) blood filter.

The blood filter according to the present invention ("blood filter 4") comprised one set consisting of 10 nonwoven filter layer compositions. The nonwoven filter layer compositions all consisted of trilobate spunbond fibers.

The prior art filter element ("filter element 2") consisted of a set of 10 filter layers made of melt blown cylindrical fibers with a diameter of 1 μm to 3 μm.

Whole blood obtained from a human donor was stored at room temperature over few hours (max 3 hours). When blood that has been stored under these conditions is filtered, platelets are in a transient activated status which promotes formation of biofilm.

To each filter element, 40 ml of whole blood were applied and the blood was filtered.

Table II depicts the results of this experiment:

| Blood filter | PLT ($10^3$/μl) in filtered whole blood[1] | WBC ($10^3$/μl) in filtered whole blood |
|---|---|---|
| Blood filter 4 | 5 (0-15)* | 0.1 (0.1-2.0) |
| Prior art | 12 (0-85) | 0.1 (0.1-2.0) |

[1]values are provided as median of 5 experiments (minimal value-maximal value)

The results of this experiment clearly show that the removal of PLTs is improved with the blood filter according to the present invention.

Experiment C

In a third experiment, the removal of contaminants as macroaggregates, clots, fat from shed blood was assessed in a prefiltration step, by applying a blood filter according to the present invention ("blood filter 5") comprising one set of 15 nonwoven filter layer compositions. The nonwoven filter layer compositions all consisted of trilobate spunbond fibers.

Two control groups were settled: one didn't include any prefiltration step, a second one included a prefiltration step which was performed through a prior art prefiltering material (needled felt). The number of layers of the prefiltering material was based on a weight equivalence.

Shed blood was obtained from patient drainages in the 6 hours after orthopedic surgery. Shed blood units were stored at room temperature over the night (max 18 hours).

In a first step, 125 to 300 ml of shed blood were applied to each of the pre-filter portions and filtration was performed by application of gravity.

Then, in a second step, the pre-filtered blood was applied on a main filter portion, consisting of one set of 20 layers of melt blown cylindrical fibers with a fiber diameter of 1 μm to 3 μm. The filtration flow was recorded.

Table III depicts the results of this experiment:

| Step I (pre-filter portion) | Step II (main filter portion) | Filtration flow [ml/min] min-max[1] |
|---|---|---|
| — | 20 layers of mb cylindrical fibers | 3.4-15.2 |
| 4 layers of polyester needled felt 400 g/m² (prior art) | 20 layers of mb cylindrical fibers | 5.9-25.2 |
| 12 layers of sb trilobate fibers (blood filter 5) 135 g/m² | 20 layers of mb cylindrical fibers | 41.6-104 |

[1]values are provided as filtration flow range, due to the high variability in shed blood volume and composition. 5 experiments were conducted for each series The results of this experiment clearly show that the removal of contaminant upstream the main filter portion improved the filtration flow when the blood filter according to the present invention was applied.

Experiment D

In experiment D filtration time and cellular removal were evaluated in scale up filtrations of red cell concentrate units. The RCC filter of the prior art, comprising a pre-filter portion consisting of two layer of 60 g/m2 thermally point bonded 100% PET spunbond (round cross section) was compared to the RCC filters according to the present invention (example I). All RCC filters tested comprised an identical main filter portion but different pre-filter portions.

Whole blood (450-500 ml) obtained from a human donor was stored at room temperature for 1-24 hours. Collected blood was centrifuged and processed with an automatic separator in order to obtain the main blood components: plasma, buffy coat and red cell concentrate. Red Cell concentrate was isolated, added by additive solution and filtered with RCC filters of the prior art and RCC filters according to the present invention (example I).

The system used for the blood collection and RCC filtration is shown in FIG. 6B (the system is described in mote detail in a section below).

Table IV depicts the results of this experiment (means±Standard Deviations):

| Blood filter | N | Filtration Time (minutes) | WBC residual ($\times 10^6$/Unit) | PLT residual ($\times 10^9$/Unit) |
|---|---|---|---|---|
| RCC filter Example I | 20 | 13 ± 2 | 0.018 ± 0.013 | 0.20 ± 0.46 |
| RCC Filter Prior art | 100 | 20 ± 5 | 0.025 ± 0.027 | 0.36 ± 1.02 |

The results of this experiment show that filtration time are improved with the blood filter according to the present invention, while leukodepletion performances are comparable.

In the following sections, preferred embodiments of blood filters according to the present invention are given. The blood filters are schematically depicted in FIGS. 5a, 5b and 5c. Each blood filter comprises a housing 1, an inlet 2 and an outlet 3. The housing 1 of the blood filter accommodates one or more sets 4a, 4b, 4c, 4d, 4e of nonwoven fiber layers 5, wherein each set 4a, 4b, 4c, 4d, 4e comprises at least one fiber layer 5. The at least one set is disposed between the inlet 2 and the outlet 3 for filtering a fluid being communicated from the inlet 2 to the outlet 3. In case of more than one set, the fluid passes the set nearest to the inlet 2 (the first set 4a) first, and than subsequently, if present, the following sets (second set 4b, third set 4c, . . . ) until it passes the outlet 3. The housing 1 is a preferably soft housing made from plastic. However, a rigid housing can be also used. In case of more than one layer 5, the layers 5 are under at least a slight compression, which is, in this case, exerted by the housing 1, so that gaps between adjacent layers 5 are prevented.

Example 1—"Soft RCC #1"

A first embodiment of a blood filter according to the invention comprises three sets 4a, 4b, 4c of non woven filter layers, see FIG. 5a. The first set 4a consists of one layer of 100% PET, thermal point bonded spunbond trilobate fibers with a basis weight of 100 g/m², a diameter of 40-45 μm (5.1 dtex) and a typical diameter of each single lobe of about 17 pm. The trilobate fibers, due to their shape, have three grooves with theoretically infinite length (i.e., extending over the whole length of the fibre. The absence of the groove has to be considered a fibers defect) and a depth of approximately 10 μm (see FIG. 2). The second set 4b consists of eighteen layers of 50 g/m² 100% PBT meltblown round fibers, which are surface modified for improving CWST, with an average diameter of approximately 2 μm. The third set 4c consists of twelve layers of 50 g/m² 100% PBT meltblown round fibers, which are surface modified for improving CWST, with an average diameter of approximately 2 μm, and which calendared for reducing fiber-to-fiber distance.

This blood filter is especially adapted for removing WBC from RCC (red cell concentrate. The first and second set 4a, 4b provide for pre-filtration and filtration, the third set 4c provides for selective filtration and "polishing" (i.e., the filtering step, in which the last residual leukocytes are removed).

In an alternative embodiment, another layer of the type of set 4a (100% PET, thermal point bonded spunbond trilobate fibers with a basis weight of 100 g/m², a diameter of 40-45 μm (5.1 dtex) and a typical diameter of each single lobe of about 17 μm) could be added as last layer after set 4c for welding process optimisation.

In a further alternative embodiment, set 4a of the three sets 4a, 4b, 4c of example 1 consists of four layers of thermal flat bonded 30 g/m², 100% PET, 2.3 dpf (denier per filament) trilobate spunbond.

In a further alternative embodiment, set 4a of the three sets 4a, 4b, 4c of example 1 consists of six layers of thermal point bonded 10 g/m², 100% nylon 6,6, 7 dpf (denier per filament) trilobate spunbond.

Example 2—"Rigid WB #1"

According to a second embodiment, the blood filter comprises five sets 4a, 4b, 4c, 4d, 4e of nonwoven filter layers, see FIG. 5b. The first set 4a consists of one layer of 100% PET, thermal point bonded spunbond trilobate fibers with a basis weight of 100 g/m², a diameter of 40-45 μm (5.1 dtex) and a typical diameter of each single lobe of about 17 μm. The trilobate fibers, due to their shape, have three grooves with theoretically infinite length and a depth of approximately 10 μm (see FIG. 2). The second set 4b consists of two layers of 50 g/m² 100% PBT meltblown round fibers with an average diameter of approximately 3 μm. The third set 4c consists of 4 layers of 50 g/m² 100% PBT meltblown round fibers, which are surface modified for improving CWST, and with an average diameter of approximately 2 μm. The fourth set 4d consists of 8 layers of 50 g/m² 100% PBT meltblown round fibers, which are surface modified for improving CWST, with an average diameter of approximately 2 μm. The fifth set 4e consists of 28 layers of 50 g/m² 100% PBT meltblown round fibers, which are surface modified for improving CWST, with an average diameter of approximately 2 μm. As housing, a rigid plastic housing is used.

This blood filter is especially adapted for removing WBC from WB (whole blood). The first, second and third set 4a, 4b, 4c provide for pre-filtration, the third, fourth and fifth set 4d, 4e provide for increasing selective filtration. Between the sets 4c, 4d, and 4e a gradient in CSWT and fiber-to-fiber distance is in place, increasing CSWT and reducing fiber-to-fiber distance in direction of the fluid flow from the inlet 2 to the outlet 3.

Example 3—"Soft RCC PRP #1"

The first set 4a consists of one layer of 100% PET, thermal point bonded spunbond trilobate fibers with a basis weight of 100 g/m², a diameter of 40-45 μm (5.1 dtex) and a typical diameter of each single lobe of about 17 μm. The trilobate fibers, due to their shape, have three grooves with theoretically infinite length and a depth of approximately 10 μm (see FIG. 2). The second set 4b consists of 4 layers of 100% PBT meltblown trilobate fibers with a basis weight of 35 g/m², a diameter of 16 μm. The trilobate fibers have three grooves with a theoretically infinite length and a depth of about 4 μm. The third set 4c consists of eighteen layers of the same layers as used in the second set of example 1, but with reduced CWST. The fourth set 4d consists of twelve layers of the same layers as used in the third set of Example 1.

This blood filter is especially adapted for removing WBC from RCC (red cell concentrate) and more specifically obtained from the PRP (Platelet Rich Plasma) procedure. The first and second set 4a, 4b provide for pre-filtration, the third and fourth set 4c, 4d provides for selective filtration. By using first fibers also in the second set 4b, cells, especially platelets, can be entrapped in a larger volume, which results in a better distribution of such cells.

Example 4—"Soft RCC PRP #2"

In a fourth embodiment of a blood filter, comprising four sets of filter layers, the third set 4c consists of sixteen layers of 100% PBT meltblown trilobate fibers with a basis weight of 50 g/m², a diameter of about 8 μm The trilobate fibers have three grooves with a theoretically infinite length and a depth of about 2 μm. For the rest, the blood filter according to the fourth embodiment equals the blood filter of the third embodiment.

This blood filter is especially adapted for removing WBC from RCC (red cell concentrate) and WB (whole blood). The first, second and third set 4a, 4b, 4c provide for pre-filtration, the fourth set 4d provides for selective filtration. By using first fibers also in the third set 4c, the distribution of captured cells can be further improved, reducing volume loss in comparison to Example 3.

Example 5—"Soft RCC PRP #3"

In a fifth embodiment of a blood filter, comprising four sets of filter layers, the third set 4c consists of sixteen layers of 100% PBT meltblown trilobate fibers with a basis weight of 50 g/m², a diameter of about 8 μm The trilobate fibers have three grooves with a theoretically infinite length and a depth of about 2 μm. The fourth set 4d of the third embodiment consists of ten layers of calendered 100% PBT meltblown trilobate fibers with a basis weight of 50 g/m², a diameter of about 8 μm. The trilobate fibers have three grooves with a theoretically infinite length and a depth of about 2 μm For the rest, the blood filter according to the fifth embodiment equals the blood filter of the third embodiment.

This blood filter is especially adapted for removing WBC from RCC (red cell concentrate). The first, second and third set 4a, 4b, 4c provide for pre-filtration, the fourth set 4d provides for selective filtration. By using first fibers also in the fourth set 4d, the distribution of captured cells can be further improved, reducing total volume loss and increasing Hemoglobin recovery.

The filter material of the blood filters of the embodiments one to five, comprising or consisting of the respective sets, is also suitable to use for filtering salvage or shed blood.

Example 6—"Rigid WB #2"

In a sixth embodiment of a blood filter, comprising five sets of filter layers, the second set 4b consists of two layers of 100% PBT meltblown trilobate fibers with a basis weight of 50 g/m², a diameter of about 8 µm. The trilobate fibers have three grooves with a theoretically infinite length and a depth of about 2 µm. For the rest, the blood filter according to the sixth embodiment equals the blood filter of the second embodiment.

This blood filter is especially adapted removing WBC from WB (Whole Blood).

Example 7—"Rigid WB #3"

In a seventh embodiment of a blood filter, comprising five sets of filter layers, the second set 4b consists of two layers of 100% PBT meltblown trilobate fibers with a basis weight of 50 g/m², a diameter of about 8 µm. The trilobate fibers have three grooves with a theoretically infinite length and a depth of about 2 µm. The third set 4c consists of four layers of 100% PBT meltblown trilobate fibers with a basis weight of 50 g/m², a diameter of about 8 µm. The trilobate fibers have three grooves with a theoretically infinite length and a depth of about 2 µm. The fourth set 4d consists of eight layers 100% bicomponent blend made of 80% PBT and 20% (polyalkylglycol terephthalate) meltblown trilobate fibers with a basis weight of 50 g/m², a diameter of about 6 µm, without any surface modifier. The trilobate fibers have three grooves with a theoretically infinite length and a depth of about 1.5 µm. For the rest, the blood filter according to the seventh embodiment equals the blood filter of the second embodiment.

This blood filter is especially adapted for removing WBC from WB (Whole Blood).

Example 8—"Soft WB #1"

In an eighth embodiment of a blood filter, comprising five sets of filter layers and a soft housing, the first set 4a consists of one layer of one layer of 100% PET, thermal point bonded spunbond trilobate fibers with a basis weight of 100 g/m², a diameter of 40-45 µm (5.1 dtex) and a typical diameter of each single lobe of about 17 µm. The trilobate fibers, due to their shape, have three grooves with theoretically infinite length and a depth of approximately 10 µm (see FIG. 2). The second set 4b consists of ten layers of 100% PBT meltblown trilobate fibers with a basis weight of 50 g/m², a diameter of about 8 µm. The trilobate fibers have three grooves with a theoretically infinite length and a depth of about 2 µm. The third set 4c consists of twentyfive calendered layers of sheat/core bicomponent PET/PE meltblown trilobate fibers, with a basis weight of 30 g/m² and a diameter of 4 µm. The trilobate fibers of the third set have three grooves with a theoretically infinite length and a depth of 1.3 µm. For the rest, the blood filter according to the eighth embodiment equals the blood filter of the second embodiment.

This blood filter is especially adapted removing WBC from WB (Whole Blood).

Example 9—"Soft PLT #1"

In a ninth embodiment of a blood filter, comprising three sets of filter layers and a soft housing, the first set 4a consists of one layer of one layer of surface modified 100% PET, thermal point bonded spunbond trilobate fibers with a basis weight of 100 g/m², a diameter of 40-45 µm (5.1 dtex) and a typical diameter of each single lobe of about 17 µm. The trilobate fibers, due to their shape, have three grooves with theoretically infinite length and a depth of approximately 10 µm (see FIG. 2). The second set 4b consists of six layers of 50 g/m² 100% PBT meltblown round fibers, which are surface modified for improving CWST, with an average diameter of approximately 2 µm. The third set 4c consists of nine layers of the layers used for the second set 4b, but with being calendered to reduce porosity.

This blood filter is especially adapted for filtering solutions with platelets, for example, for filtering platelet rich plasma or a platelet concentrate. Platelets are allowed to pass through the filtering material (surface chemistry reduces PLT adhesion), the second and third set are adapted for WBC depletion.

Example 10—"Soft PLT #2"

In a tenth embodiment of a blood filter, comprising three sets of filter layers and a soft housing, the second set 4b consists of twenty layers of bicomponent blend made of 80% PBT and 20% (polyalkylglycol terephthalate) meltblown trilobate fibers, with a weight of 40 g/m², a diameter of 8 µm. The trilobate fibers of the second set have three grooves with a theoretically infinite length and a depth of 2 µm. For the test, the blood filter according to the tenth embodiment equals the blood filter of the ninth embodiment.

This blood filter is especially adapted for filtering solutions with platelets, for example, for filtering plasma or a platelet concentrate. Platelets are allowed to pass through Platelets are allowed to pass through the filtering material (surface chemistry reduces PLT adhesion), the second and third set are adapted for WBC depletion.

Example 11—"Soft Plasma #1"

In an eleventh embodiment of a blood filter according to the invention the blood filter comprises two sets 4a, 4b of non woven filter layers. The first set 4a consists of one layer of 100% PET, thermal point bonded spunbond trilobate fibers with a basis weight of 100 g/m², a diameter of 40-45 µm (5.1 dtex) and a typical diameter of each single lobe of about 17 µm. The trilobate fibers, due to their shape, have three grooves with theoretically infinite length and a depth of approximately 10 µm (see FIG. 2). The second set 4b consists of thirty layers of calandered 50 g/m² 100% PBT meltblown round fibers, which are surface modified for improving CWST, with an average diameter of approximately 2 µm.

This blood filter is especially adapted for filtering plasma.

Example 12—"Shed Blood #1"

In a twelfth embodiment of a blood filter, the blood filter comprises a series of 2 rigid housings (see FIG. 6C). The first housing accommodates a single set, which consists of 20 layers of 100 g/m² 100% PBT trilobite meltblown fibers, which are surface modified for improving CWST, with an average diameter of approximately 16 µm and a typical groove depth of about 4 µm. The second housing accommodates a filtering material as given in Example 2.

This filtering material in the first housing is assessed as prefiltration step which could promote the blood flow through the main filter portion of the second housing, allowing a good leukodepletion performance. (see FIG. 6C).

This blood filter is intended for the removal of contaminants as macroaggregates, clots, fat or fibrin degradation products from shed blood drained in the first 6 hours after a surgery. See experiment C for details.

Prefiltration and filtration step could be combined in only one filter consisting of a filter composed of 4-6 different prefiltration stages.

Example 13—"Shed Blood #2"

In a thirteenth embodiment of a blood filter, the blood filter comprises a single layer of 100% PET, thermal point bonded spunbond trilobate fibers with a basis weight of 100 g/m$^2$, a diameter of 40-45 µm (5.1 dtex) and a typical diameter of each single lobe of about 17 µm. The trilobate fibers, due to their shape, have three grooves with theoretically infinite length and a depth of approximately 10 µm (see FIG. 2). According to the present invention, such a blood filter could be applied in the shed blood processing system (FIG. 7). The blood filter 10 is arranged in the rigid collection container in the form of a sieving pocket. The aim is to remove contaminants as macroaggregates, clots, fat or fibrin degradation products from shed blood directly during the suction and collection of shed blood from a surgery wound. The prefiltered shed blood is then transferred to a main filter portion 11 for the cellular removal (for example, white blood cells and/or platelets).

As an alternative, instead of meltblown fibers, bicomponent "island in the sea" fibers could be also used. Furthermore, it is not mandatory that only fiber layers are being used in the blood filter. It is also possible to combine them with other types of filter material, like membranes, textiles (i.e. materials from micro-yarns), or nets, to give some examples. Finally, it is not mandatory that all fiber layers, especially in the prefiltration stages, are nonwovens: microsieves obtained whether by extrusion (nets) or weaving of technical yarns can be used instead.

In the following sections different preferred embodiments of systems processing whole blood, salvage blood or at least one blood components are given. Each system includes at least one blood filter according to the invention, wherein the filter is arranged between a first reservoir and a second reservoir.

The system depicted in FIG. 6A is a system for processing of whole blood. The system comprises a first bag 20 (i.e. a first reservoir), in which whole blood is provided for filtration. In addition, an anticoagulant can be provided in the first bag 20. The first bag 20 is linked, in fluid flow communication, to a blood filter 10 through a first conduit-means 21, typically a flexible plastic tube. The first conduit-means 21 is connected with the blood filter 10 at the inlet port 2 of the blood filter housing 1. The blood filter 10 is connected with a second conduit means 22 at the outlet port 3 of the blood filter housing 1. The blood filter 10 is thus linked, in fluid-flow communication with a second bag 23 (i.e. a second reservoir) through the second conduit means 22 and an inlet port 28 of the second bag 23. The second bag is, by means of an outlet port 24 and a y-connector 25, linked to a third bag 26 and a fourth bag 27. Furthermore, the system comprises an additional fluid line 29 between the first bag 20 and the second bag 23, which allows transferring fluid from the second bag 23 to the first bag 20 without having to pass the blood filter 10. The system allows transferring whole blood from the first bag 20 to the second bag 23, passing the filter 10 for WBC and platelet removal. Within the second bag 23, blood can be further separated by, for example, centrifugation. The plasma part can be transferred to the fourth bag 24. Additive solution, which is contained in the third bag 26, can be transferred to the second bag 23 to improve the storage of the remaining RCC (red cell concentrate). As blood filter 10, filters given in examples 2, 6, 7, 8 are preferred.

The system depicted in FIG. 6B is a system for filtering RCC. The system comprises a first bag 40 for whole blood collection, filled with an anticoagulant, which is connected by means of flexible tubes on one side to a second bag 41 for storing plasma, and on the opposite side to a third bag 42 for transfer. The third bag 42 is connected to a fourth bag 43 for storing RBC (red blood cells), the bag 43 being filled with an additive storage solution. Furthermore, the system comprises a blood filter 10 which is arranged between the third bag 42 and fourth bag 43 so that fluid, which is being transferred from the third bag 42 to the fourth bag 43, must pass the blood filter 10. Whole blood collected in the first bag 40 can be separated by centrifugation. The plasma part can be transferred to the second bag 41. The remaining part, comprising the RBC, can be transferred, via the third bag and the blood filter 10, to the fourth bag 43 for storage purposes. The blood filter 10 is adapted for removing WBC and platelets. As blood filter 10, filters given in examples 1, 3, 4, 5 are preferred.

The system depicted in FIG. 6c is a system to process shed blood. The system comprises a first bag 60 for collecting shed blood and a second bag 61 for accommodating the processed blood. The first bag 60 is linked to the second bag 61 by flexible tubes for transferring the blood from the first bag 60 to the second bag 61. Furthermore, the system comprises a blood filter 10 which arranged between the first bag 60 and the second bag 61 so that fluid, which is being transferred from the first bag 60 to the second bag 61, must pass the blood filter 10. In this case, the blood filter 10 comprises a first and a second housing being in fluid communication by means of a tube. The second housing is arranged downstream of the first housing, so that blood, which is transferred from the first bag 60 to the second bag 61, first passes the first housing and afterwards passes the second housing. As blood filter 10, filter given in example 12 is preferred. The at least one set of fiber layers for prefiltration is arranged in the first housing, the sets of fiber layers for main filtration are arranged in the second housing.

The system depicted in FIG. 7 is a further system to process shed blood. The system comprises a rigid container 80 for both receiving shed blood and collecting the processed blood. The systems further comprises a blood filter 10 in the form of a sieving pocket, which is arranged in the rigid container, separating the container in a first reservoir 81 for receiving the shed blood and a second reservoir 82 for receiving the processed blood which has passed the blood filter 10. The system can comprise, in addition, means 83, for example a tube and a connector, for transferring fluid from the second reservoir to a blood bag 84 for storage purposes. A second blood filter 11 can be arranged downstream in the fluid line providing a second filtration stage before the blood is collected in the blood bag 84. As blood filter 10, filter given in example 13 is preferred, while for filter 11 anyone of examples used for WB (FIG. 6a) can be used.

In the embodiments presented above, fibers with a smooth surface, which have been obtained by extrusion, where used. The surface roughness of the fibers Ra (average roughness) is Ra equal or less than 0.1 µm, preferably Ra equal or less than 0.03 µm, most preferably Ra equal or less than 0.01 µm.

The invention claimed is:

1. A blood filter comprising an inlet, an outlet, at least two sets of filter layers disposed between the inlet and the outlet for filtering a fluid being communicated between the inlet and the outlet, each layer comprising at least first nonwoven fibers, wherein each of the first fibers comprises at least one groove extending in the longitudinal direction of the fiber, and at least one filter housing exerting a compressive force on the at least two sets of filter layers sufficient to prevent gaps between the filter layers, the at least one filter housing being a soft housing and/or a hard housing accommodating the at least two layers.

2. A blood filter according to claim 1, wherein the first fibers have a lobate shape.

3. A blood filter according to claim 1, wherein the groove has a length of at least 10 µm.

4. A blood filter according to claim 1, wherein the diameter of the first fibers is in the range of 2 to 50 µm.

5. A blood filter according to claim 1, wherein the first fibers are spunbond fibers and/or meltblown fibers.

6. A blood filter according to claim 1, wherein each of the layers comprises at least 20% weight percent of first fibers.

7. A blood filter according to claim 1, wherein the at least first and second set are arranged such that fluid flowing from the inlet to the outlet passes the first set before passing the second set, each set comprising at least one filter layer, wherein the two adjacent filter layers of two subsequent sets are different in their properties.

8. A blood filter according to claim 7, wherein the first set comprises at least one layer with first fibers, the first fibers having a groove with a depth in the range of 5 µm to 15 µm.

9. A blood filter according to claim 7, wherein the second set comprises at least one layer with first fibers, the first fibers having a groove with a depth in the range of 0.2 µm to 5 µm.

10. A blood filter according to claim 7, wherein the first set and the second set comprise at least one layer comprising first fibers, wherein the diameter of first fibers in the first set is greater than the diameter of first fibers in the second set.

11. A blood filter according to claim 7, wherein the first set and the second set are arranged in a single housing.

12. A blood filter according to claim 7 wherein the first set and the second set are arranged in different housings, the housings being in fluid communication.

13. The blood filter according to claim 1 wherein each of the first fibers has an average surface roughness of less than 0.1 µm.

14. A method of using a filter according to claim 10 for the removal of substances from whole blood or blood components, comprising flowing blood components selected from the group consisting of cell salvage blood, whole blood, red cell concentrate, platelet rich plasma, platelet concentrate and plasma through the filter.

15. A system for processing whole blood, salvage blood or at least one blood component, including at least one filter according to claim 1, wherein the filter is arranged between a first reservoir and a second reservoir.

16. A method of using a system according to claim 15, for the removal of substances from whole blood or blood components, comprising flowing blood components selected from the group consisting of cell salvage blood, whole blood, red cell concentrate, platelet rich plasma, platelet concentrate and plasma from the first reservoir through the filter and into the second reservoir.

17. A blood filter comprising an inlet, an outlet, at least a first set and second set of filter layers, and at least one filter housing exerting a compressive force on the at least two sets of filter layers sufficient to prevent gaps between the filter layers, the at least one filter housing being a soft housing and/or a hard housing accommodating the at least two layers, wherein the at least first and second set are arranged such that fluid flowing from the inlet to the outlet passes the first set before passing the second set, each set comprising at least one filter layer, wherein the two adjacent filter layers of two subsequent sets are different in their properties, each set of filter layers comprises at least one layer of nonwoven fibers, at least a part of the fibers of the layer are first fibers, each of the first fibers comprises at least one groove extending in the longitudinal direction of the fiber, and the first fibers in the first set of filter layers having a groove with a depth in the range of 5 µm to 15 µm and the first fibers in the second set of filter layers having a groove with a depth in the range of 0.2 µm to 5 µm.

\* \* \* \* \*